US008041421B2

(12) United States Patent
Birchall et al.

(10) Patent No.: US 8,041,421 B2
(45) Date of Patent: Oct. 18, 2011

(54) TRANSDERMAL DELIVERY SYSTEM FOR POLYNUCLEOTIDES

(75) Inventors: James Birchall, Cardiff (GB); Galit Levin, Nordiya (IL); Amikam Gershonowitz, Modi'in (IL)

(73) Assignee: TransPharma Medical Ltd., Lod (IL)

( * ) Notice: Subject to any disclaimer, the term of this patent is extended or adjusted under 35 U.S.C. 154(b) by 689 days.

(21) Appl. No.: 10/597,431

(22) PCT Filed: Jan. 25, 2005

(86) PCT No.: PCT/IL2005/000089
§ 371 (c)(1),
(2), (4) Date: Sep. 17, 2007

(87) PCT Pub. No.: WO2005/069736
PCT Pub. Date: Aug. 4, 2005

(65) Prior Publication Data
US 2008/0114281 A1    May 15, 2008

Related U.S. Application Data

(60) Provisional application No. 60/626,479, filed on Nov. 10, 2004.

(30) Foreign Application Priority Data

Jan. 25, 2004    (IL) .......................................... 160033

(51) Int. Cl.
*A61N 1/30* (2006.01)
*A61M 31/00* (2006.01)
(52) U.S. Cl. .......................................... 604/20; 604/500
(58) Field of Classification Search .................... 604/20, 604/500
See application file for complete search history.

(56) References Cited

U.S. PATENT DOCUMENTS

| 4,699,880 | A   |   | 10/1987 | Goldstein ................. 435/172.2 |
| 5,749,847 | A   |   | 5/1998  | Zewert et al.                          |
| 6,009,345 | A   |   | 12/1999 | Hofmann                                |
| 6,148,232 | A   | * | 11/2000 | Avrahami ....................... 604/20 |
| 6,429,200 | B1  | * | 8/2002  | Monahan et al. ........... 514/44 R    |
| 6,527,716 | B1  |   | 3/2003  | Eppstein                               |

(Continued)

FOREIGN PATENT DOCUMENTS

WO    2004/039427    5/2004

(Continued)

OTHER PUBLICATIONS

Chesnoy, S. and Huang, L. (2002) Enhanced cutaneous gene delivery following intradermal injection of naked DNA in a high ionic strength solution. Molecular Therapy: the journal of the American Society of Gene Therapy 5(1):57-62.

(Continued)

*Primary Examiner* — Kevin C Sirmons
*Assistant Examiner* — Bradley Osinski
(74) *Attorney, Agent, or Firm* — Winston & Strawn LLP

(57) ABSTRACT

A system for intradermal or transdermal delivery of oligonucleotides or polynucleotides and methods of use thereof employ an apparatus that generates micro-channels in the skin of a subject in conjunction with a pharmaceutical composition comprising an oligonucleotide or polynucleotide, wherein the oligonucleotide or polynucleotide can be delivered into the organism through the micro-channels. The system and methods achieve expression of target proteins encoded by the polynucleotides, and hence are useful in immunization and gene therapy.

14 Claims, 13 Drawing Sheets

U.S. PATENT DOCUMENTS

| | | |
|---|---|---|
| 6,597,946 B2 | 7/2003 | Avrahami ............... 604/20 |
| 6,611,706 B2 | 8/2003 | Avrahami ............... 604/20 |
| 6,615,079 B1 | 9/2003 | Avrahami ............... 604/20 |
| 6,708,060 B1 | 3/2004 | Avrahami ............... 604/20 |
| 6,711,435 B2 | 3/2004 | Avrahami ............... 604/20 |
| 7,505,812 B1* | 3/2009 | Eggers et al. ............ 604/20 |
| 2003/0208152 A1* | 11/2003 | Avrahami et al. ........ 604/20 |
| 2005/0287217 A1* | 12/2005 | Levin et al. ............ 424/486 |

FOREIGN PATENT DOCUMENTS

WO 2004/039428 5/2004

OTHER PUBLICATIONS

Federoff, Howard J. et al., (1992) Expression of nerve growth factor in vivo from defective herpes simplex virus 1 vector prevents effects of axotomy on sympathetic ganglia. Proc. Natl. Acad. Sci. USA 89:1636-1640.

Fink, D. J. et al., (1996) Gene transfer to neurons using herpes simplex virus-based vectors. Annu Rev Neurosci 19:265-287.

Hengge, Ulrich R. et al., (1996) Expression of naked DNA in human, pig, and mouse skin. J. Clinical Investigation 97(12):2911-16.

Moon, Chulso et al., (2003) Current status of gene therapy for lung cancer and head and neck cancer. Clin. Cancer Res. 9(14):5055-5067.

Sintov, Amnon C. et al., (2003) Radiofrequency-driven skin microchanneling as a new way for electrically assisted transdermal delivery of hydrophilic drugs. J. Control Release 89(2):311-320.

Uhlmann, Eugen and Peyman, Anusch (1990) Antisense oligonucleotides: a nev therapeutic principle. Chemical Reviews 90(4):543-584.

* cited by examiner

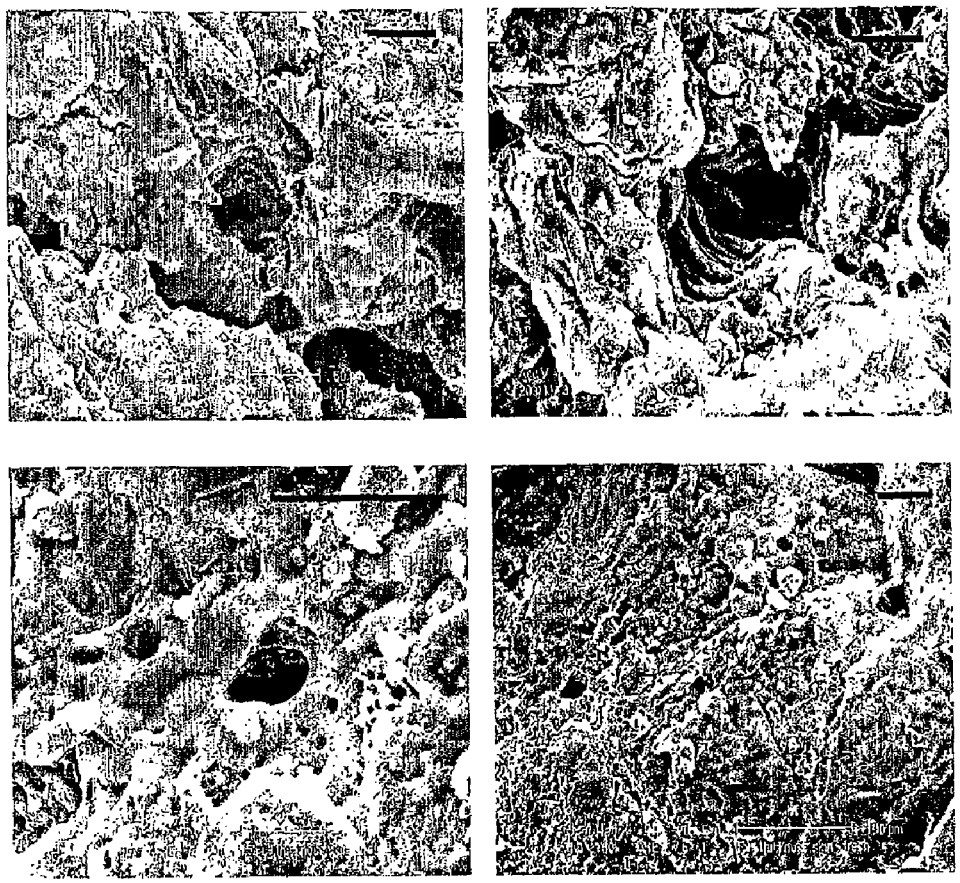
FIG. 1
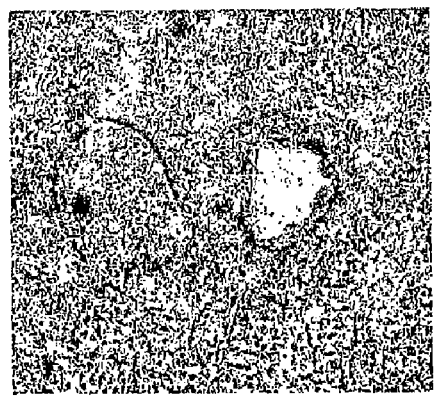 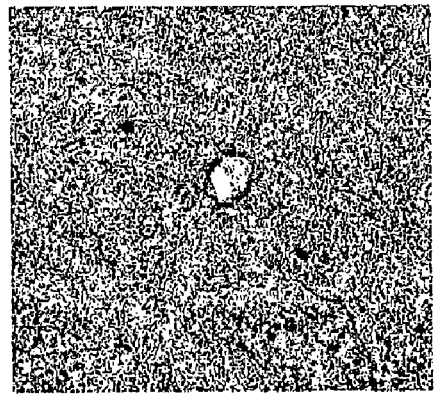
FIG. 2A          FIG. 2B

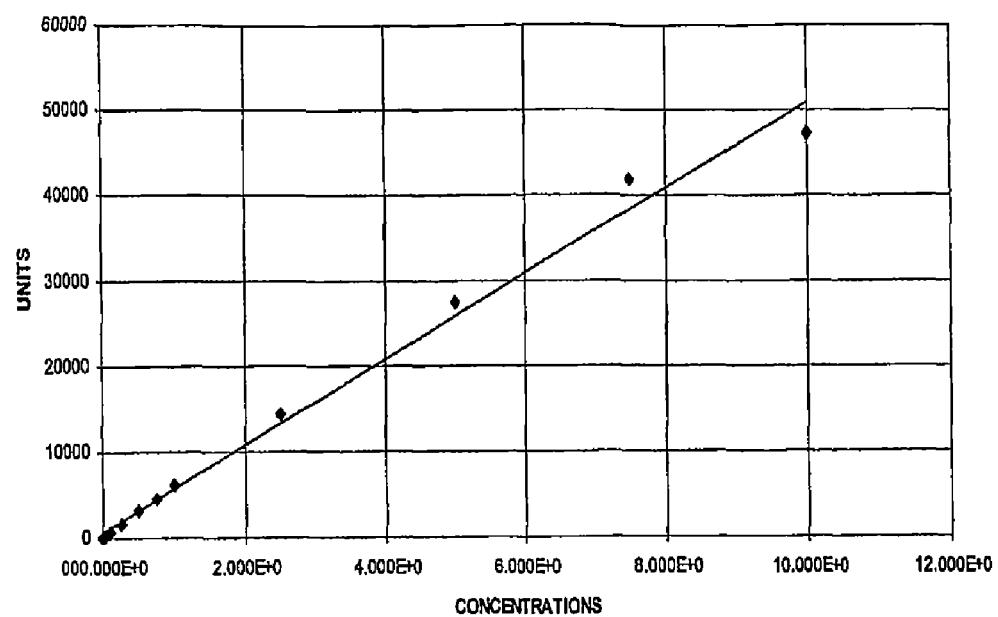
FIG. 4
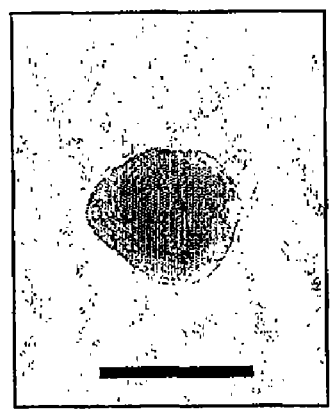 
FIG. 5A  FIG. 5B

FIG. 8A
FIG. 8B
FIG. 9A
FIG. 9B
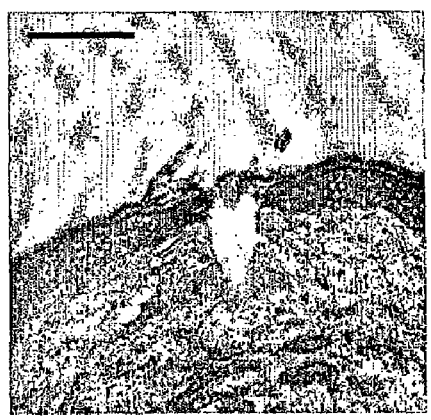
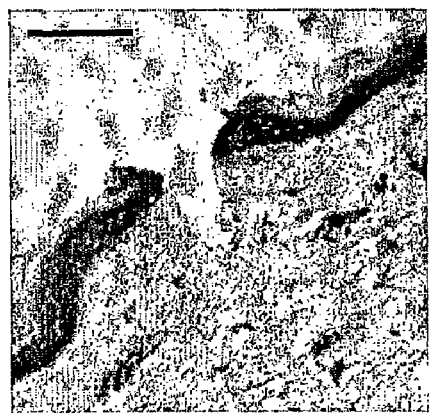
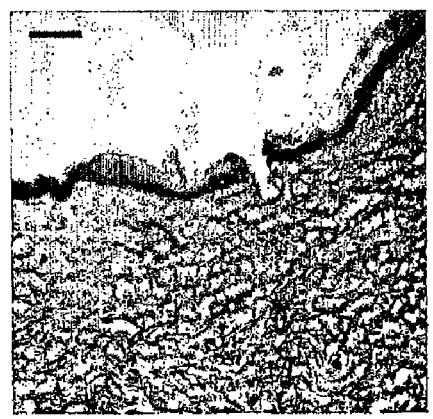
FIG. 9C

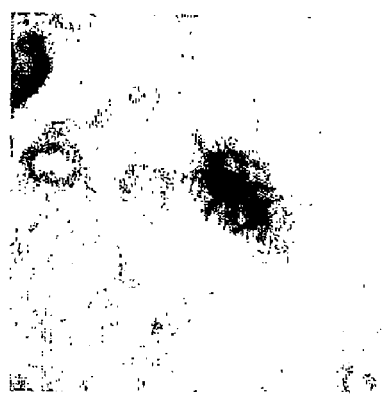 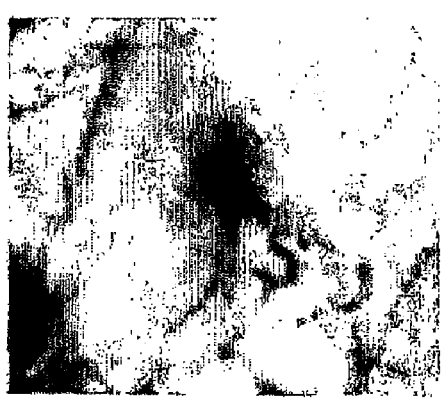
FIG. 14A  FIG. 14B
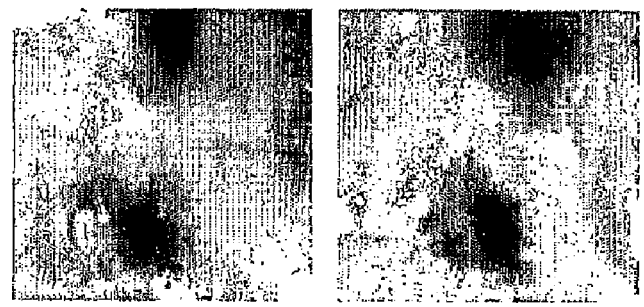
FIG. 15

FIG. 18A   FIG. 18B
FIG. 18C  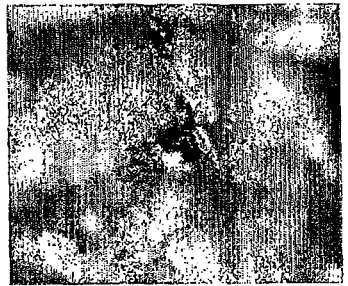 FIG. 18D
FIG. 18E  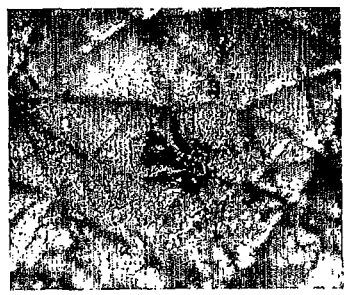 FIG. 18F
FIG. 18G   FIG. 18H

TRANSDERMAL DELIVERY SYSTEM FOR POLYNUCLEOTIDES

This invention is a 371 of PCT/IL05/00089 filed Jan. 25, 2005 which claims priority to U.S. provisional application 60/626,479 filed Nov. 10, 2004. This invention also claims priority to Israeli application 160033 filed Jan. 25, 2004.

FIELD OF THE INVENTION

The present invention relates to a system comprising an apparatus that generates micro-channels in the skin of a subject in conjunction with a pharmaceutical composition comprising an oligonucleotide or polynucleotide, wherein the oligonucleotide or polynucleotide are delivered into the skin through the micro-channels generated. The system and methods of the present invention achieve expression of target proteins in the skin of the subject, and are useful in immunization and gene therapy.

BACKGROUND OF THE INVENTION

The direct introduction of a biologically active polypeptide into the cells of a patient can have significant therapeutic value. However, this approach also has several drawbacks. Of primary concern is the risk of potential toxicities, particularly at dosages sufficient to produce a biological response to the polypeptide. The clinical impact of a polypeptide is also limited by its relatively short half-life in vivo, which usually results from its degradation by proteases present in the target tissue. Moreover, polypeptides, which are injected into a tissue typically enter the blood circulation before they have a significant therapeutic effect on the tissue into which they were injected.

For these reasons, gene therapy is envisioned as a potentially definitive treatment for a variety of diseases or clinical conditions including cancer, genetic disorders, immune diseases, cardiovascular diseases, viral infections, and in clinical transplantation.

Clinical trials aimed at restoring defective genes are currently proposed for treating cancer. Thus, in lung cancer and in head and neck cancer, for example, clinical trials for restoration of defective p53 have consistently showed evidence of p53 gene transduction and expression, and apoptosis (Moon et al. (2003) Clin. Cancer Res. 9: 5055-5067). Similarly, patients with severe combined immunodeficiency (SCID) treated with adenosine deaminase gene have shown significant immune reconstitution leading to protective immunity (Engel et al. (2003) Curr. Opin. Mol. Ther. 5: 503-507).

Additionally, silencing of undesired genes using antisense oligonucleotides or inhibitory RNA (e.g., siRNA, miRNA, RNAi) directed against these genes also offers much hope for the treatment of a variety of diseases. For example, over expression of many growth factors was found to be correlated with cancer development. Antisense oligonucleotides against such growth factors have been shown to be useful in ameliorating cancer growth (Hirai et al. (2003) J. Gene Med. 5: 951-957).

It is clear, however, that gene therapy can be improved further. Promising avenues include improved gene delivery systems, design of immunogen and anti-angiogenesis gene therapies, design of interfering RNA, and adjuvant use of gene therapy.

U.S. Pat. No. 5,749,847 to Zewert et al. discloses a method for delivering a nucleotide into an organism. The method includes applying a composition containing a nucleotide to epidermis of an organism, and then electroporating the epidermis so as to cause at least a portion of the composition to pass across the epidermis and hence delivering the nucleotide to the organism.

U.S. Pat. No. 6,009,345 to Hofmann provides an apparatus and methods for transdermal delivery of drugs or genes that combine electroporation and iontophoresis. While electroporation forms new pathways through the stratum corneum, iontophoresis provides the driving force necessary to transport the drugs or genes through these pathways into the underlying tissue.

U.S. Pat. No. 6,527,716 to Eppstein discloses a method of delivering a nucleic acid into an organism, which includes ablating a biological membrane by the use of a heat conducting element and thereby porating the membrane in a selected area, applying an electromagnetic field to the selected area, and then contacting the selected area with a nucleic acid under conditions whereby the electromagnetic field actively induces the flux of the nucleic acid into the organism. Thus, ablating and forming micro pores in a biological membrane according to U.S. Pat. No. 6,527,716 involves a heat element that is held in contact with the biological membrane, and as the heat element absorbs energy it causes thermal ablation of the biological membrane, and the nucleic acid is delivered into the organism driven by the electromagnetic field.

There remains an unmet need for efficient apparatus and methods for intradermal or transdermal delivery of polynucleotides, which do not require the provision of a driving force for the delivery of the polynucleotides.

SUMMARY OF THE INVENTION

The present invention relates to an effective system for intradermal or transdermal delivery of oligonucleotides or polynucleotides. The present invention further relates to a system and methods for ablating the stratum corneum of the skin and intradermally or transdermally delivering oligonucleotides or polynucleotides to the pretreated skin. The system and methods achieve expression of target proteins encoded by the polynucleotides, and hence are very useful in immunization and gene therapy.

It is now disclosed that generation of micro-channels in an area of the skin of a subject by the apparatus of the present invention and subsequent application of a composition comprising a polynucleotide to the treated skin achieves expression of a polypeptide encoded by the polynucleotide. It is further disclosed that the intradermal or transdermal delivery of the polynucleotide and the expression of the polypeptide encoded by that polynucleotide is enhanced if micro-channels are generated not only before but also after the polynucleotide application. Alternatively, the expression of the polypeptide encoded by the polynucleotide is also achieved by application of a composition comprising a polynucleotide on an area of skin of a subject and subsequently generating micro-channels in said area of the skin of the subject.

It is further disclosed that the diameter of the micro-channels generated by the apparatus of the present invention are in the range of several microns to tens of microns. This range of dimensions enables large polynucleotides to be transported through the micro-channels and delivered into the organism. The depth of the micro-channels generated in the skin of a subject depends inter alia upon the length of the electrodes of the apparatus. Thus, while micro-channels generated by 100-micron length electrodes penetrate through the stratum corneum into the underlying dermis, micro-channels generated by 50-micron length electrodes reside solely in the epidermis. The micro-channels generated in the skin using the apparatus of the present invention are of dimensions sufficient to provide enhanced flux of polynucleotides in the absence of any electromagnetic field.

It is now disclosed that the transport of the polynucleotides through the micro-channels generated in the stratum corneum into the underlying tissues results in the expression of a target protein encoded by the polynucleotide. It should be appreciated that the advantage of the apparatus of the invention resides in the formation of hydrophilic micro-channels, which permit transport of hydrophilic polynucleotides. Thus, the present invention does not require the use of liposomes to promote polynucloetide delivery and expression. According to the present invention, expression of a target protein is accomplished successfully with "naked" polynucleotides (not complexed to lipids or provided in liposomes). Yet, the present invention is also useful with polynucleotides complexed with lipids.

According to one aspect, the present invention provides a method for intradermal or transdermal delivery of an oligonucleotide or polynucleotide comprising: (a) generating at least one micro-channel in an area of the skin of a subject; and (b) applying to the area where the at least one micro-channel is present a pharmaceutical composition comprising as an active ingredient a therapeutically effective amount of an oligonucleotide or polynucleotide and a pharmaceutically acceptable carrier.

According to some embodiments, the method for intradermal or transdermal delivery of the oligonucleotide or polynucleotide comprises: (a) generating at least one micro-channel in an area of the skin of a subject; (b) applying to the area where the at least one micro-channel is present a pharmaceutical composition comprising as an active ingredient a therapeutically effective amount of an oligonucleotide or polynucleotide and a pharmaceutically acceptable carrier; and (c) generating a plurality of micro-channels in said area of the skin of the subject, thereby promoting the intradermal or transdermal delivery of the oligonucleotide or polynucleotide.

According to the principles of the present invention, the oligonucleotide or polynucleotide administered to the subject is selected from the group consisting of oligonucleotides or polynucleotides of DNA and oligonucleotides or polynucleotides of RNA. According to additional embodiments, the DNA is selected from genomic DNA, complementary DNA (cDNA), and synthetic DNA, and the RNA is selected from mRNA and synthetic RNA, in a single stranded or double stranded form.

According to some embodiments, the oligonucleotide or polynucleotide encodes a polypeptide, protein, fragment, analog, or a fusion protein thereof. According to certain embodiments, the oligonucleotide or polynucleotide encodes a therapeutic or immunogenic polypeptide selected from the group consisting of insulin, proinsulin, follicle stimulating hormone, insulin like growth factor-1, insulin like growth factor-2, platelet derived growth factor, epidermal growth factor, fibroblast growth factors, nerve growth factor, colony stimulating factors, transforming growth factors, tumor necrosis factor, calcitonin, parathyroid hormone, growth hormone, bone morphogenic protein, erythropoietin, hemopoietic growth factors, luteinizing hormone, glucagon, glucagon like peptide-1, anti-angiogenic proteins, clotting factors, anti-clotting factors, atrial natriuretic factor, plasminogen activators, bombesin, thrombin, enkephalinase, vascular endothelial growth factor, interleukins, viral antigens, non-viral antigens, transport proteins, and antibodies.

According to additional embodiments, the oligonucleotide or polynucleotide administered to the subject is operably linked to regulatory sequences, thereby said polynucleotide is capable of being expressed in cells of said subject.

The methods of the present invention are thus advantageous in replacement therapy in which expression of a therapeutic protein is required. The methods of the present invention are also advantageous in RNA silencing such as in antisense therapy in which transcription and/or translation of a mutated or other detrimental protein should be arrested.

According to some embodiments, the oligonucleotide is selected from the group consisting of antisense oligonucleotides, small interfering oligonucleotides (siRNAs), micro RNAs (miRNAs), repeat associated RNAs (rasiRNA), and any other oligonucleotides known in the art, which inhibit transcription and/or translation of a mutated or other detrimental protein. The antisense oligonucleotide may comprise at least 15 nucleotides in length. Alternatively, the antisense oligonucleotide may comprise at least 21 nucleotides in length. According to additional embodiments, the oligonucleotide is double stranded RNA (dsRNA) oligonucleotides. According to certain embodiments, the dsRNA oligonucleotides are small interfering RNA (siRNA) oligonucleotides. The siRNA oligonucleotide may comprise at least 15 nucleotides in length. Alternatively, the siRNA sequence may comprise at least 21 nucleotides in length. The miRNAs are single stranded RNAs, which form a hairpin loop. According to other embodiments, the oligonucleotide is capable of increasing or eliciting immunogenicity of proteins.

According to additional embodiments, the pharmaceutical composition comprising the oligonucleotide or polynucleotide further comprising at least one additive selected from the group consisting of lipids, polycations, and nuclease inhibitors. The pharmaceutical compositions according to the principles of the present invention may comprise two or more oligonucleotides, polynucleotides, or combination thereof.

It should be appreciated that the methods of the present invention encompass intradermal and transdermal delivery of oligonucleotides or polynucleotides. Thus, oligonucleotides or polynucleotides can be delivered locally to cells adjacent to the micro-channels generated according to the principles of the present invention and/or can be delivered transdermally to the blood circulation.

According to some embodiments, generating the at least one micro-channel in the area of the skin of the subject is performed by inducing ablation of the stratum corneum using the devices disclosed in the following patents: U.S. Pat. Nos. 6,148,232; 6,597,946; 6,611,706; 6,711,435; 6,708,060; and 6,615,079; the contents of which are incorporated herein in their entirety by reference. It is, however, emphasized that although some preferred embodiments of the present invention relate to intradermal or transdermal delivery obtained by ablating the skin by the devices referred herein above, substantially any method known in the art for generating micro-channels in the skin of a subject may be used.

According to additional embodiments, generating the at least one micro-channel in the area of the skin of the subject is performed by an apparatus comprising:
  (a) an electrode cartridge comprising a plurality of electrodes; and
  (b) a main unit comprising a control unit, which is adapted to apply electrical energy between two or more electrodes when the electrodes are in vicinity of the skin, enabling ablation of stratum corneum in an area beneath said electrodes, thereby generating at least one micro-channel.

According to other embodiments, the control unit of the apparatus comprises circuitry to control the magnitude, frequency, and/or duration of the electrical energy delivered to the electrodes, so as to control the current flow or spark generation, and thus the width, depth and shape of the one or more formed micro-channels. Preferably, the electrical energy is at radio frequency.

According to additional embodiments, the electrode cartridge comprising the plurality of electrodes, which form an electrode array, is adapted to generate a plurality of micro-channels having uniform shape and dimensions. Preferably, the electrode cartridge is removable.

According to some embodiments, the diameter of the electrodes is in the range of 30 to 150 microns. According to certain exemplary embodiments, the diameter of the electrodes within an electrode array is in the range of 40 to 100 microns. According to other embodiments, the length of the electrodes is in the range of 30 to 500 microns. According to some embodiments, the length of the electrodes is in the range of 40 to 150 microns. According to a certain exemplary embodiment, the electrodes within an electrode array are of a 50-micron length.

According to another aspect, the present invention provides a method for transdermal delivery of an oligonucleotide or polynucleotide comprising: (a) applying to an area of the skin of a subject a pharmaceutical composition comprising as an active ingredient a therapeutically effective amount of an oligonucleotide or polynucleotide according to the principles of the present invention; and (b) generating at least one micro-channel in the area of the skin of the subject according to the principles of the present invention, thereby promoting the intradermal or transdermal delivery of the oligonucleotide or polynucleotide.

According to a further aspect, the present invention provides a system for intradermal or transdermal delivery of an oligonucleotide or polynucleotide comprising an apparatus for facilitating intradermal or transdermal delivery of an oligonucleotide or polynucleotide through the skin of a subject, and a pharmaceutical composition comprising an oligonucleotide or polynucleotide, the apparatus comprising:

(a) an electrode cartridge comprising a plurality of electrodes; and (b) a main unit comprising a control unit, which is adapted to apply electrical energy between two or more electrodes when the electrodes are in vicinity of the skin, enabling ablation of stratum corneum in an area beneath said electrodes, thereby generating at least one micro-channel.

According to other embodiments, the control unit of the apparatus comprises circuitry to control the magnitude, frequency, and/or duration of the electrical energy delivered to the electrodes, so as to control the current flow or spark generation, and thus the width, depth and shape of the one or more formed micro-channels. Preferably, the electrical energy is at radio frequency.

According to additional embodiments, the electrode cartridge comprising the plurality of electrodes, which form an electrode array, is adapted to generate a plurality of micro-channels having uniform shape and dimensions. Preferably, the electrode cartridge is removable.

According to some embodiments, the diameter of the electrodes is in the range of 30 to 150 microns. According to certain exemplary embodiments, the diameter of the electrodes within an electrode array is in the range of 40 to 100 microns. According to other embodiments, the length of the electrodes is in the range of 30 to 500 microns. According to some embodiments, the length of the electrodes is in the range of 40 to 150 microns. According to a certain exemplary embodiment, the electrodes within an electrode array are of a 50-micron length.

These and other embodiments of the present invention will be better understood in relation to the figures, description, examples, and claims that follow.

BRIEF DESCRIPTION OF THE FIGURES

FIG. 1 shows scanning electron micrographs of RF-micro-channels in intact human skin. Bar=50 µm.

FIGS. 2A-B show light micrographs of RF-micro-channels in heat-separated epidermal membrane. A, Original magnification=×200; B, Original magnification=×100.

FIG. 4 shows a calibration curve for calculation of donor concentrations of fluorescent nanoparticles. $R^2$=0.990.

FIGS. 5A-B show transmission electron micrographs showing the validity for using fluorescent nanoparticles as a diffusive model for lipid:polycation:DNA (LPD) non-viral gene therapy vectors. A, LPD 3:2:1 w/w vector; B, Fluorescent nanoparticle. Bar=100 nm.

FIGS. 8A-B show light micrographs of methylene blue stained skin following ViaDerm treatment. A, Original magnification=×40; B, Original magnification=×100.

FIGS. 9A-C show light micrographs of human breast skin treated with ViaDerm parameter setting of 330V, 3 bursts, 700 µsec, 140 electrodes. A, Eosin stained, original magnification=×200; B, Toludine blue stained, original magnification=×200; C, Toludine blue stained, original magnification=×100. Bar=100 µm.

FIGS. 14A-B show light photomicrographs of heat-separated epidermal membrane stained for β-galactosidase expression. A, Original magnification=×100; B, Original magnification=×200.

FIG. 15 shows light photomicrographs of tape-stripped ViaDerm-treated human skin stained for β-galactosidase expression. Original magnification=×100.

FIG. 18A-H show light micrographs of three different samples of human skin stained for β-galactosidase expression after ViaDerm application, DNA coating and then an additional ViaDerm application. A, Sample 1: Original Magnification=×40; B, Sample 1: Original Magnification=×100; C, Sample 2: Original Magnification=×40; D, Sample 2: Original Magnification=×100; E, Sample 3: Original Magnification=×40; F, Sample 3: Original Magnification=×40; G, Sample 3: Original Magnification=×100; H, Sample 3: Original Magnification=×100.

DETAILED DESCRIPTION OF THE INVENTION

Figure 3A:
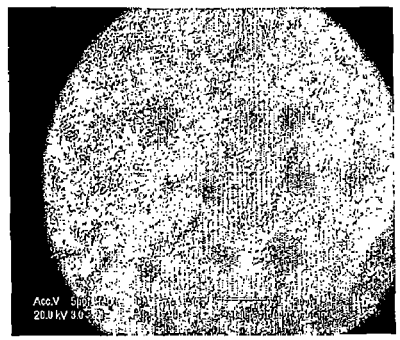
FIGS. 3A-F show scanning electron micrographs of RF-micro-channels in heat-separated epidermal membrane. A, scanning electron micrograph at low magnification showing distribution pattern of channels following 2 applications of ViaDerm; B-D, scanning electron micrograph at high magnification showing dimensions of micro-channels; E-F, scanning electron visualization of micro-channel depth using an angled electron beam (Bar (where added)=50 µm).
Figure 3B:
Figure 3C:
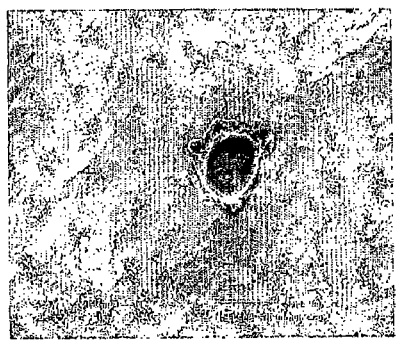
Figure 3D:
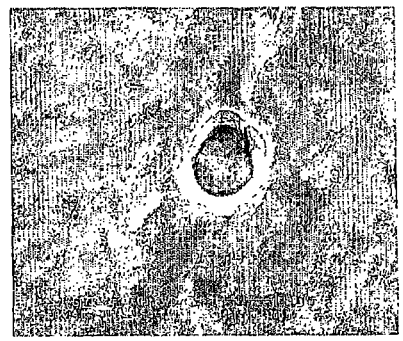
Figure 3E:
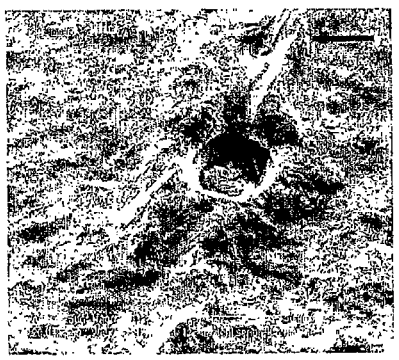
Figure 3F:
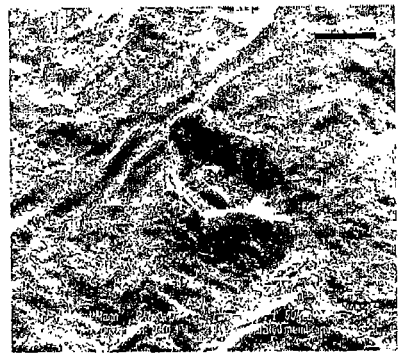

The present invention provides a transdermal delivery system for an oligonucleotide or polynucleotide comprising an apparatus that generates hydrophilic pathways within the stratum corneum at an area of the skin of a subject and a pharmaceutical composition, which comprises at least one oligonucleotide or polynucleotide. As oligonucleotides and polynucleotides are hydrophilic molecules, the system of the invention is particularly useful in transdermal gene therapy.

Preparation of Polynucleotides

As used herein "oligonucleotide" or "polynucleotide" refers to polymers of deoxyribonucleotides, ribonucleotides, and modified forms thereof in the form of a separate fragment or as a component of a larger construct, in a single strand or in a double strand form. The polynucleotides to be used in the invention include sense and antisense oligonucleotides or polynucleotides of DNA or RNA as appropriate to the goals of the therapy practiced according to the invention. The DNA or RNA molecules may be complementary DNA (cDNA), genomic DNA, synthesized DNA or a hybrid thereof or an RNA molecule such as mRNA. Accordingly, as used herein, the terms "construct", "gene construct" "polynucleotide" and "oligonucleotide" are meant to refer to both DNA and RNA molecules. The term "oligonucleotide" refers to a polymer having not more than 50 nucleotides in length while the term "polynucleotide" refers to a polymer having more than 50 nucleotides in length. For sake of brevity, the term polynucleotides is used throughout the specification and includes both oligonucleotides and polynucleotides.

An "isolated polynucleotide" refers to a polynucleotide segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to polynucleotides, which have been substantially purified from other components, which naturally accompany a nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding an additional polypeptide sequence.

The term "encoding" refers to the inherent property of specific sequences of nucleotides in an isolated polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a polynucleotide encodes a protein if transcription and translation of mRNA corresponding to that polynucleotide produces the protein in a cell.

Oligonucleotides or polynucleotides for use in the invention can be obtained using hybridization methods well known in the art. DNA and RNA sequences may also be synthesized using automated nucleic acid synthesis equipment well known in the art. Use of the well-known polymerase chain reaction (PCR) is particularly preferred for generating mixtures of polynucleotides. Genomic nucleic acids may be prepared by means well known in the art such as the protocols described in Ausubel, et al., Current Protocols in Molecular Biology, Chapters 2 and 4 (Wiley Interscience, 1989). cDNA can be synthesized according to means well known in the art (see, e.g., Maniatis, et al., Molecular Cloning; A Laboratory Manual, Cold Spring Harbor Lab, New York, 1982).

One who is skilled in the art will appreciate that more than one nucleic acid may encode any given protein in view of the degeneracy of the genetic code and the allowance of exceptions to classical base pairing in the third position of the codon, as given by the so-called "Wobble rules." Moreover, polynucleotides that include more or less nucleotides can result in the same or equivalent proteins. Accordingly, it is intended that the present invention encompass all polynucleotides that encode a polypeptide or a protein.

Preferred polynucleotides for use in the present invention may encode for therapeutic or immunogenic peptides, polypeptides, proteins, or fragments, analogs, and fusion proteins thereof. The term "polypeptide" used throughout the specification and claims includes peptides, polypeptides and proteins. The immunogenic polypeptides can act as antigens to provoke a humoral and/or cellular response. The polynucleotides can also encode for antibodies. In this regard, the term "antibody" encompasses whole immunoglobulin of any class, chimeric antibodies, hybrid antibodies with dual or multiple antigen specificities and fragments including hybrid fragments. Also included within the meaning of "antibody" are conjugates of such fragments, and so-called antigen binding proteins (single chain antibodies). The encoded antibodies can also be anti-idiotypic antibodies (antibodies that bind other antibodies) as described, for example, in U.S. Pat. No. 4,699,880.

Therapeutic peptides, polypeptides and proteins according to the invention include, but are not limited to, insulin; proinsulin; follicle stimulating hormone; insulin like growth factor-1 and insulin like growth factor-2; platelet derived growth factor; epidermal growth factor; fibroblast growth factors; nerve growth factor; transforming growth factors; tumor necrosis factor; calcitonin; parathyroid hormone; growth hormone; bone morphogenic protein; erythropoietin; hemopoietic growth factors; luteinizing hormone; glucagon; glucagon-like peptide 1; clotting factors such as factor VIIIC, factor IX, tissue factor, and von Willebrand factor; anti-clotting factors such as Protein C; atrial natriuretic factor; lung surfactant; plasminogen activators such as urokinase or tissue-type plasminogen activator, including human tissue-type plasminogen activator (t-PA); bombesin; thrombin, enkephalinase; collagen; mullerian-inhibiting agent; relaxin A-chain; relaxin B-chain; prorelaxin; inhibin; activin; vascular endothelial growth factor; anti-angiogenic proteins (such as platelet factor 4, IP-10); receptors for hormones or growth factors; integrins; protein A or D; rheumatoid factors; neurotrophic factors such as bone-derived neurotrophic factor (BDNF), neurotrophin-3, -4, -5, or -6 (NT-3, NT-4, NT-5, or NT-6); CD proteins such as CD-3, CD-4, CD-8, and CD-19; osteoinductive factors; immunotoxins; interferons such as interferon-$\alpha$, -$\beta$, and -$\gamma$; colony stimulating factors (CSFs) such as M-CSF, GM-CSF, and G-CSF; interleukins (ILs) such as IL-1 to IL-10; superoxide dismutase; T-cell receptors; surface membrane proteins; decay accelerating factor; viral antigens such as, for example, a portion of the AIDS envelope; transport proteins; homing receptors; addressins; regulatory proteins; antibodies; and analogs or fragments thereof so long as the analogs and fragments thereof retain the therapeutic or immunogenic activity of the naturally occurring polypeptides.

The term "analog" as used herein refers to a peptide, polypeptide, or protein in which one or more amino acid residues have been replaced by different amino acids. It will be understood that a polynucleotide encoding naturally occurring peptide, polypeptide or protein as listed herein above may be prepared synthetically so as to include variations in nucleotides. Such polynucleotides yield peptide-, polypeptide-, or protein analogs, which are encompassed in the present invention so long as the peptide, polypeptide or protein analogs retain the therapeutic or immunogenic activity of the naturally occurring peptides, polypeptides or proteins.

The term "fusion protein" as used herein denotes a protein comprising at least two covalently bound peptides, polypeptides, proteins, or a combination thereof. A fusion protein may comprise a polypeptide capable of increasing the immunogenicity of another polypeptide such as, for example, GM-CSF, which is capable of eliciting an immune response. Alternatively or additionally, the fusion protein may comprise an antibody specific for a receptor so as to increase the specificity of binding of a ligand to the receptor. Alternatively or additionally, the fusion protein may comprise a tag so as to improve detection or to increase expression of the fusion protein.

The present invention encompasses oligonucleotides that comprise CpG nucleotide sequences capable of increasing protein immunogenicity.

Those of skill in the art will, however, appreciate that the methods of the invention may be adapted for use in administering any oligonucleotide, polynucleotide, or mixture thereof, which encode therapeutic and/or immunogenic peptides of interest. The invention is therefore not limited to use with any particular polynucleotide or oligonucleotide.

The oligonucleotides or polynucleotides of the invention may contain a modified internucleoside phosphate backbone to improve the bioavailability and hybridization properties of the oligonucleotide or polynucleotide. Linkages are selected from the group consisting of phosphodiester, phosphotriester, methylphosphonate, phosphoroselenoate, phosphorodiselenoate, phosphoroanilothioate, phosphoroanilidate, phosphoramidate, phosphorothioate, phosphorodithioate or combinations thereof.

Additional nuclease linkages include alkylphosphotriester such as methyl- and ethylphosphotriester, carbonate such as carboxymethyl ester, carbamate, morpholino carbamate, 3'-thioformacetal, silyl such as dialkyl ($C_1$-$C_6$)- or diphenylsilyl, sulfamate ester, and the like. Such linkages and methods for introducing them into oligonucleotides are described in many references, e.g. reviewed generally by Peyman and Ulmann, Chemical Reviews, 90:1543-584 (1990).

The oligonucleotide or polynucleotide may be part of a gene construct or an expression vector. The term "gene construct" or "expression vector" refers to a DNA or RNA molecule that comprises an oligonucleotide or polynucleotide which encodes a target protein and which includes initiation and termination signals operably linked to regulatory elements including a promoter and polyadenylation signal capable of directing expression in the cells of a subject. Thus, a gene construct or an expression vector contains the necessary regulatory elements operably linked to the polynucleotide that encodes a target protein, such that when present in a cell of the individual, the polynucleotide will be expressed.

The regulatory elements necessary for gene expression of a DNA molecule include: a promoter, an initiation codon, a stop codon, and a polyadenylation signal. In addition, enhancers are often required for gene expression. It is necessary that these elements be operably linked to the polynucleotide that encodes the target protein such that the polynucleotide can be expressed in the cells of a subject and thus the target protein can be produced.

Initiation codons and stop codons are generally considered to be part of a gene construct comprising the polynucleotide that encodes the target protein. However, it is necessary that these elements will be functional in the subject to whom the polynucleotide is administered.

Examples of promoters useful for practicing the present invention include, but are not limited to, promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV), promoters from human genes such as human actin, human myosin, human hemoglobin, human muscle creatine and human metalothionein and tissue-specific promoters such as involucrin, keratin 5, and keratin 14. Suitable protocols for use of promoters in construction of gene constructs are well known in the art (see, for example, Current Protocols in Molecular Biology, Chapter 1, Wiley Interscience, 1989) and are exemplified herein below.

Examples of polyadenylation signals useful for practicing the present invention include, but are not limited to, SV40 polyadenylation signals and LTR polyadenylation signals.

In addition to the regulatory elements required for DNA expression, other elements may also be included in the gene construct. Such additional elements include enhancers. The enhancer may be selected from the group including, but not limited to, human actin, human myosin, human hemoglobin, human muscle creatine and viral enhancers such as those from CMV, RSV and EBV.

Gene constructs can be provided with mammalian origin of replication in order to maintain the construct extrachromosomally and produce multiple copies of the construct in the cell. Plasmids pCEP4 and pREP4, for example, from Invitrogen (San Diego, Calif.) contain the Epstein Barr virus origin of replication and nuclear antigen EBNA-1 coding region, which produce high copy episomal replication without integration. Other plasmids known in the art such as, for example, pCMV may be used so long as the gene constructs express the target protein encoded by the polynucleotide. Alternatively, expression vectors known to the skilled artisan may be used for practicing the present invention. Examples of expression vectors include viral vectors such as adeno-associated viral vectors (Berns et al., 1995, Ann. N.Y. Acad. Sci. 772:95-104), adenoviral vectors, herpes virus vectors (Fink et al., 1996, Ann. Rev. Neurosci. 19:265-287), packaged amplicons (Federoff et al., 1992, Proc. Natl. Acad. Sci. USA 89:1636-1640), papilloma virus vectors, picornavirus vectors, polyoma virus vectors, retroviral vectors, SV40 viral vectors, vaccinia virus vectors, and the like.

In order to be a functional gene construct, the regulatory elements must be operably linked to the polynucleotide that encodes the target protein. Accordingly, it is necessary for the initiation and termination codons to be in frame with the isolated polynucleotide that encodes the target protein.

By inserting one or more polynucleotide sequences of interest into a gene construct, along with another gene, which encodes, for example, a ligand for a receptor on a specific target cell, the gene construct is now target specific. Preferred targeting is accomplished by using an antibody to target the gene construct. Those of skill in the art will know of, or can readily ascertain without undue experimentation, specific polynucleotide sequences which can be inserted into the gene construct to allow target specific delivery of the gene construct containing the polynucleotides of interest.

Early work showed that polycations such as polylysine and DEAE-dextran promote the uptake of proteins and single- and double-stranded polynucleotides into animal cells. For example, polylysine-based vectors have been extensively tested for gene transfer. Thus, the present invention also encompasses synthetic DNA-delivery systems.

According to some embodiments of the invention, introducing a polynucleotide to a subject's skin is accomplished by lipid complexing rather than by the "naked" polynucleotide sequence. Lipids that are used for promoting DNA delivery are well known in the art and selected from phospholipids, e.g., phosphatidylethanolamines and phosphatidylcholines such as 1,2-dioleoyl-sn-glycero-3-phosphoethanolamine, 1,2-diphytanoyl-sn-glycero-3-phosphoethanolamine, and 1,2-dimyristoyl-glycero-3-phosphoethanolamine, and the like. In an exemplary embodiment, the lipid is 1,2-Dioleoyl-3-trimethylammonium-propane. The present invention thus encompasses polynucleotide compositions wherein the composition comprises one or more lipids. According to the present invention, the lipids may be mixed or combined with a polynucleotide in a number of ways to produce a variety of compositions of non-covalently bonded macroscopic structures, e.g., liposomes, multilamellar vesicles, unilamellar vesicles, micelles, and simple films. The polynucleotide and lipids can be mixed in a variety of molar ratios. A protocol for complexation of a polynucleotide, a lipid, and a polycation is exemplified herein below (see Example 7). However, other additives as known in the art may be added to the pharmaceutical compositions of the invention so long as the polynucleotide is capable of being expressed within cells of a treated subject.

It should be appreciated that the introduction of a gene construct comprising a polynucleotide encoding a target protein that is operably linked to regulatory sequences brings about the expression of the target protein in cells of a treated subject. This may be used in replacement therapy in which a gene encoding a target protein is introduced into target cells of a subject, thus resulting in the production of the protein necessary to forestall development of a disorder associated with a deficiency of this protein. This may also be used in replacement therapy in which a mutant gene is expressed within target cells of a subject and a wild type gene is introduced into the target cells, thus resulting in the production of the wild type protein necessary to forestall development of the disorder associated with the mutant protein.

Another particular advantage of the invention will be its use in antisense therapy. Thus, where a particular disorder is associated with the expression of a particular mutated DNA sequence, a polynucleotide that interferes with the specific expression of the mutated gene at the transcriptional or translational level can be used. This approach utilizes, for example, antisense nucleic acid and/or ribozymes to block transcription or translation of a specific mutated mRNA, either by masking that mRNA with an antisense nucleic acid or by cleaving it with a ribozyme.

Thus, antisense nucleic acids are DNA or RNA molecules that are complementary to at least a portion of a specific mRNA molecule (Weintraub, Scientific American, 262:40, 1990). As such, in the cell, the antisense nucleic acids hybridize to the corresponding MRNA, thus forming a double-stranded molecule. The antisense nucleic acids interfere with the translation of the mRNA, since the cell will not translate an MRNA that is double-stranded. To date, several genes and oncogenes have been targeted for suppression or down-regulation by antisense nucleic acids including, but not limited to, p53, ras, fos, and myc.

Ribozymes are RNA molecules possessing the ability to specifically cleave other single-stranded RNA in a manner analogous to DNA restriction endonucleases. Through the modification of polynucleotides that encode these RNAs, it is possible to engineer molecules that recognize specific polynucleotides associated with production of a mutated proto-oncogene or tumor suppressor gene in an RNA molecule and cleave it. A major advantage of this approach is that, because ribozymes are sequence-specific, only target mRNAs with particular mutant sequences are inactivated.

RNA silencing has been extensively studied. Double stranded RNA (dsRNA), and more particularly small interfering RNA (siRNA), were found to be highly selective and sequence-specific inhibitors of endogenous genes. The present invention thus encompasses double stranded RNA (dsRNA), and more particularly small interfering RNA (siRNA). According to some embodiments, the siRNA sequences comprise at least 15 nucleotides. According to other embodiments, the siRNA comprise at least 21 nucleotides. The present invention further encompasses microRNAs (miRNAs), repeat associated siRNAs (rasiRNAs), and any other known oligonucleotides, which interfere with transcription and/or translation of a mutated protein.

Pharmaceutical Compositions

The pharmaceutical compositions of the invention comprise a therapeutically effective amount of at least one oligonucleotide or polynucleotide of the invention.

The pharmaceutical composition further comprises a pharmaceutical acceptable carrier or diluent. The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic agent is administered. Carriers are more or less inert substances when added to a pharmaceutical composition to confer suitable consistency or form to the composition.

As used herein a "pharmaceutically acceptable carrier" may be aqueous or non-aqueous solutions, suspensions, or emulsions. Examples of aqueous carriers include water, saline and buffered media, alcoholic/aqueous solutions, emulsions or suspensions. The pharmaceutical composition may also comprise additives such as albumin to prevent adsorption to surfaces, anti-oxidants (e.g., ascorbic acid, sodium metabisulfite), stabilizers (e.g., monosaccharides and disaccharides such as glucose, galactose, and sucrose) and preservatives (e.g., Thimerosal, benzyl alcohol, parabens, m-cresol). Pharmaceutically acceptable salts of a polynucleotide are also included in the present invention. Salts derived from inorganic bases include sodium, potassium, lithium, ammonium, calcium, magnesium, zinc, and the like. Salts derived from pharmaceutically acceptable organic non-toxic bases include salts of primary, secondary, and tertiary amines, basic amino acids, and the like.

The pharmaceutical composition may also include hydrophilic polymers. The hydrophilic polymers may increase the half-lives of the polynucleotides of the invention and hence increase their bioavailability. Examples of hydrophilic polymers include, but not limited to, cellulose, hydroxy cellulose, carboxymethyl cellulose, hydroxyethyl cellulose, hydroxypropyl cellulose, hydroxypropylmethyl cellulose, polysaccharides, chitin, chitosan, diacylated chitin, gum acacia, agarose, carrageenan, gelatin, gum tragacanth, alginate, karaya gum, veegum, pectin, hyaluronic acid, maltodextrin, polyvinylpyrrolidone, polyglycolic acid, polyoxyethylene, polyoxypropylene, polyacrylates, and methacrylate polymers.

The pharmaceutical composition may further include at least one nuclease inhibitor to prevent the polynucleotide of the invention from being degraded by nucleases, e.g., aurintricarboxylic acid (ATA).

The pharmaceutical composition may also include at least one protein or polypeptide. For example, the large T-antigen nuclear localization signal is a protein that binds DNA and facilitates its transport into the nucleus of the cell. Thus, the combination of a polynucleotide according to the invention and a protein known to enhance DNA transport is encompassed in the present invention.

The pharmaceutical composition may further comprise other ingredients including, but not limited to, polycations and lipids. Examples of polycations are polylysine, DEAE-dextran, protamine sulfate, and the like. Examples of lipids are phospholipids such as phosphatidylethanolamines and phosphatidylcholines, and the like.

The formulation of the pharmaceutical composition comprising a therapeutically effective amount of an oligonucleotide or polynucleotide according to the present invention is determined so as to provide improved stability of the oligonucleotide or polynucleotide while retaining or improving its bioavailability.

The pharmaceutical composition may be formulated as an aqueous solution. Alternatively, the pharmaceutical composition may be formulated in a dry or lyophilized formulation. Alternatively or additionally, the composition may be formulated in a medical patch as known in the art (see, for example, PCT/IL03/00903 and PCT/IL03/00902, the content of which is incorporated by reference as if fully set forth herein). The pharmaceutical composition may be formulated in a form of a film, or a gel using, for example, Carbopol® 940 and triethanolamine as gelling agents, or the pharmaceutical composition may be formulated in any other suitable form, which enables transdermal delivery of the polynucleotides of the invention.

The dosage of each polynucleotide to be administered to a subject using the method of the invention will vary depending on the desired response and the polynucleotide used.

The dosage of the polynucleotide may be modified to achieve therapeutic levels of expression. Means to confirm the presence of DNA or RNA and quantity of expressed proteins are well known to those skilled in the art. Some of such means are illustrated in the Examples provided herein below; generally, they include immunoassays (such as enzyme-linked immnunosorbent assays), PCR techniques, and immunohistological analyses performed according to techniques well known in the art. Dosages of the administered polynucleotides can be adjusted to achieve the desired level of expression based on information provided by these detection and quantification means as well as on in vivo clinical signs known to practitioners skilled in the clinical art.

Devices for Enhancing Transdermal Delivery of Polynucleotides

The system of the present invention comprises an apparatus for enhancing intradermal or transdermal delivery of a polynucleotide. According to the principles of the present invention, the apparatus is used to generate at least one micro-channel through which a hydrophilic pharmaceutical composition is delivered efficiently through the skin of a subject into the body.

The term "micro-channel" as used in the context of the present patent application refers to a pathway, generally extending from the surface of the skin through all or significant part of the stratum corneum, through which molecules can diffuse.

According to some embodiments, the present invention incorporates the techniques for creating micro-channels by inducing ablation of the stratum corneum using electrical energy, including the devices disclosed in the following patents: U.S. Pat. Nos. 6,148,232; 6,597,946; 6,611,706; 6,711,435; 6,708,060; and 6,615,079; the contents of which is incorporated by reference as if fully set forth herein. It is however emphasized that although some preferred embodiments of the present invention relate to transdermal delivery obtained by ablating the skin by the aforementioned apparatus, substantially any method known in the art for generating micro-channels in the skin of a subject may be used.

According to certain embodiments, the apparatus for facilitating intradermal or transdermal delivery of an oligonucleotide or polynucleotide comprises: (a) an electrode cartridge comprising a plurality of electrodes; and (b) a main unit comprising a control unit which is adapted to apply electrical energy between two or more electrodes when the electrodes are in vicinity of the skin, typically generating current flow or one or more sparks, enabling ablation of stratum corneum in a region beneath said electrodes, thereby generating at least one micro-channel.

According to the principles of the invention, the electrode cartridge comprises a plurality of electrodes thus forming an electrode array, which generates upon application of an electrical energy at least one micro-channel, and preferably a plurality of micro-channels, within the subject's skin. It will be understood that the term "plurality" of electrodes refers herein to two or more electrodes. The main unit loaded with the electrode cartridge is also denoted herein ViaDerm™. Typically, however, the overall area of micro-channels generated in the stratum corneum is small compared to the total area covered by the electrode array.

According to some embodiments, the diameter of the electrodes within the electrode array is in the range of 30 to 150 microns. According to certain embodiments, the diameter is in the range of 40 to 100 microns. According to some additional embodiments, the length of the electrodes within the electrode array is in the range of 30 to 500 microns. According to other embodiments, the length of the electrodes is in the range of 40 to 150 microns. In a certain exemplary embodiment, the electrodes within the electrode array are of a 100-micron length. In another exemplary embodiment, the electrodes within the electrode array are of a 50-micron length.

According to other embodiments, the control unit of the apparatus comprises circuitry to control the magnitude, frequency, and/or duration of the electrical energy delivered to the electrodes, so as to control the current flow or spark generation, and thus the width, depth and shape of the one or more formed micro-channels. Preferably, the electrical energy delivered to the electrodes is at radio frequency.

According to a currently preferred embodiment, the electrode cartridge comprising the plurality of electrodes generates a plurality of micro-channels having uniform shape and dimensions. Preferably, the electrode cartridge is removable. More preferably, the electrode cartridge is discarded after one use, and as such it is designed for easy attachment to the main unit and subsequent detachment from the main unit.

According to further embodiments, the pressure obtained while placing the apparatus of the present invention on a subject's skin activates the electrical energy delivered to the electrodes. Such mode of action ensures that activation of electrodes occurs only in a close contact with the skin enabling the desired formation of the micro-channels.

According to the present invention, micro-channels may be formed by the application of current to the skin in order to ablate the stratum corneum by heating the cells. Spark generation, cessation of spark generation, or a specific current level may be used as a form of feedback, which indicates that the desired depth has been reached and current application should be terminated. For these applications, the electrodes are preferably shaped and/or supported in a cartridge that is conducive to facilitate formation of micro-channels in the stratum corneum to the desired depth, but not beyond that depth. Alternatively, the current may be configured so as to form micro-channels in the stratum corneum without the generation of sparks. The resulted micro-channels are uniform in shape and size.

Thus, according to the present invention, the electrodes may be maintained either in contact with the skin, or in vicinity of the skin, up to a distance of about 500 microns therefrom. According to a further embodiment, ablation of the stratum corneum is performed by applying an electrical current having a frequency between about 10 kHz and 4000 kHz, preferably between about 10 kHz and 500 kHz, and more preferably at 100 kHz.

To minimize the chance of contamination of the cartridge and its associated electrodes, attachment and detachment of the cartridge is performed without the user physically touching the cartridge. Preferably, cartridges are sealed in a sterile cartridge holder, which is opened immediately prior to use, whereupon the main unit is brought in contact with a top surface of the cartridge, so as to engage a mechanism that locks the cartridge to the main unit. A simple means of unlocking and ejecting the cartridge, which does not require the user to touch the cartridge, is also provided.

Methods for Transdermal Delivery of Polynucleotides

The present invention provides a method for transdermal delivery of an oligonucleotide or polynucleotide comprising generating at least one micro-channel in an area of the skin of a subject, and applying to the area of the skin of the subject in which the at least one micro-channel is present a pharmaceutical composition comprising a therapeutically effective amount of an oligonucleotide or polynucleotide.

The present invention further provides a method for transdermal delivery of an oligonucleotide or polynucleotide comprising the steps of: (a) generating at least one micro-channel in an area of the skin of a subject; (b) applying to the area of skin in which the at least one micro-channel is present a pharmaceutical composition comprising a therapeutically effective amount of an oligonucleotide or polynucleotide; and (c) generating at least one additional micro-channel in said area of the skin of the subject thereby promoting polynucleotide delivery.

The present invention further provides a method for transdermal delivery of an oligonucleotide or polynucleotide comprising the steps of: (a) applying to an area of skin of a subject a pharmaceutical composition comprising a therapeutically effective amount of an oligonucleotide or polynucleotide; and (b) generating at least one micro-channel in the area of skin of the subject thereby promoting polynucleotide delivery.

It should be appreciated that according to the principles of the present invention, generation of micro-channels in an area of the skin of a subject and then application of a polynucleotide composition brings about to intradermal delivery of the polynucleotide into cells or tissues surrounding or underlying the micro-channels, and to expression of a polypeptide encoded by the polynucleotide in these cells or tissues. Yet, it is particularly advantageous to generate micro-channels not only before but also after the application of the polynucleotide composition since under such conditions the polypeptide expression is higher than that achieved under conditions where micro-channels are generated only before the application of the polynucleotide composition. Alternatively, it is advantageous to apply a pharmaceutical composition comprising a polynucleotide to an area of the skin of a subject and subsequently to generate micro-channels in that area of skin. It will be understood that application of a pharmaceutical composition comprising a polynucleotide can take place immediately after generating the micro-channels or thereafter, for example, in a lag time of about 4 to 8 hours. Yet, the pharmaceutical composition can be applied even after longer lag time so long as the micro-channels remain open.

The term "therapeutically effective amount" means the amount of a polynucleotide sufficient to produce the desired effect when applied topically over the duration of intended use.

According to preferred embodiments of the invention, the method of transdermal delivery of a polynucleotide is very useful for replacement therapy, wherein a target protein encoded by the polynucleotide has to be expressed within cells of a subject, thereby producing the target protein.

According to additional embodiments of the invention, the method of transdermal delivery of a polynucleotide is highly useful in antisense therapy, wherein a mutant gene is expressed within target cells and the expression of the mutant gene causes a disease. Thus, introducing an antisense oligonucleotide abrogates the expression of the mutant gene. Additionally, the method of the present invention is also useful for transdermal delivery of small interfering RNAs (siRNAs), which are known to mediate sequence specific MRNA degradation.

The methods of the present invention thus encompass intradermal and transdermal delivery of polynucleotides. While the intradermal delivery brings about to a local delivery of a polynucleotide, particularly to sites adjacent to the micro-channels, more particularly within the epidermis and dermis, the transdermal delivery brings about to polynucleotide delivery to the blood circulation.

It will be appreciated that the methods disclosed in the present invention may be used in combination therapy with conventional methods of therapy, such as, for example, chemotherapy, radiation therapy and surgery.

Having now generally described the invention, the same will be more readily understood through reference to the following examples, which are provided by way of illustration and are not intended to be limiting of the present invention.

EXAMPLE 1

Morphology of Radio Frequency-Micro-Channels in Full-Thickness Human Skin

Materials and Methods

Tissue:

Full-thickness human breast skin was obtained from mastectomy or breast reduction with local ethical committee approval and informed patient consent. All excess adipose tissue was removed by blunt dissection. Tissue was transported in MEM (EAGLES) 25 mM HEPES growth media (Cat. No. 32360-026, Invitrogen Corporation, Paisley, UK) and used within 3 hrs of excision.

ViaDerm Parameters:

The ViaDerm™ device used in the present experiments is as disclosed in U.S. Pat. No. 6,148,232 and in Sintov, I., et al. (J. Control. Release 89: 311-320, 2003). ViaDerm parameter setting: 2 applications; Electrodes: 140; Burst length: 700 μsec; Number of bursts: 5; Trans Epidermal Water Loss (TEWL) control: 8.8 g/hm$^2$; TEWL after application(s): 11.4 g/hm$^2$ Electron Microscopy:

The samples were fixed with 2.5% glutaraldehyde in 0.1 M sodium cacodylate buffer (pH 7.4) for 1 hr at room temperature and washed for 10 min (2×5 min) in the same buffer. The samples were post-fixed in 1% osmium tetroxide in 0.1 M cacodylate buffer for 1 hr at 4° C. and then dehydrated with a graded series of ethanol concentrations as follows: 70% for 10 min at 4° C.; 100% for 10 min at 4° C.; 100% for 10 min at 4° C.; 100% for 10 min at 4° C. The samples were then transferred into a critical point drier (Samdri 780, Maryland, USA) and dried using carbon dioxide for 12 hrs. The samples were mounted on metal stubs and coated with a thin layer of pure gold using an Edward sputter coater prior to examination in a Philips XL-20 scanning electron microscope.

Results

FIG. 1 shows the structural morphology of the channels created in full-thickness breast skin following application of ViaDerm. The channels clearly appear as deep invaginations into the tissue with the width of the channel ranging from 30 to 50 μm.

EXAMPLE 2

Morphology of Micro-Channels in Heat-Separated Epidermal Membrane

The distribution pattern and dimensions of radio frequency (RF)-micro-channels in heat-separated human epidermal membrane were determined.

Materials and Methods

Tissue:

Full-thickness human skin was obtained and prepared as described in Example 1.

ViaDerm Parameters:

ViaDerm parameter setting: 2 applications; Electrodes: 140; Burst length: 700 μsec; Number of bursts: 5; TEWL control: 6.2 g/hm$^2$; TEWL after application(s): 20.6 g/hm$^2$.

Heat Separation of Skin:

Following application of the ViaDerm device the upper layers (stratum corneum and viable epidermis) of the skin were removed using the following technique: a glass container of distilled water was warmed to 60° C. and the skin sample was cut to an appropriate size for heat separation. The tissue was placed into the pre-heated container using forceps and after 55 seconds, the tissue was removed using forceps and allowed to dry. A small incision through the stratum corneum and epidermal layer was made using a scalpel. The dermis of the tissue was then gripped. At the point of incision, the epidermal and stratum corneum membrane were slowly peeled away from dermal layer. Once the membrane 'flap' was large enough, the remaining area of the membrane was removed using a gloved hand. The isolated membrane was placed in a container of distilled water at room temperature, where the membrane unfolded and floated on the surface of the water, with the stratum corneum facing upward. A piece of foil was placed underneath the membrane and the membrane was removed from the bath in its flattened form.

Light Microscopy:

The epidermal membrane was placed onto a glass microscope slide and viewed using an Olympus IX50 microscope under bright field illumination.

Electron Microscopy:

Dried heat-separated membrane was mounted on a metal stub and coated with a thin layer of pure gold using an Edward sputter coater prior to examination in a Philips XL-20 scanning electron microscope.

Results

FIG. 2 and FIG. 3 show that the RF-micro-channels either totally penetrate or partially penetrate the heat-separated epidermal membrane comprising the stratum corneum and the viable epidermis. Although the depth of the micro-channels was variable, probably due to variation in thickness of the separated membrane, the diameter of the micro-channels, approximately 50 μm, was reproducible and consistent with the micro-channel dimensions observed in full-thickness skin (FIG. 1).

EXAMPLE 3

Diffusion of Fluorescent Nanoparticles through Micro-Channels in Heat-Separated Epidermal Membrane The diffusion of fluorescent nanoparticles through ViaDerm-treated heat-separated epidermal membrane was performed. These fluorescent nanoparticles have similar particle diameter to non-viral gene therapy vectors. In addition, it was aimed at determining whether the diffusion characteristics depend on the parameter setting employed and whether the skin has to be analyzed fresh or following frozen storage.

Materials and Methods

Tissue:

Fresh full-thickness human skin was obtained and prepared as described in Example 1. In addition, a skin sample that had been obtained and transported in the same way prior to freezing at −20° C. for 6 weeks was defrosted at room temperature.

ViaDerm Parameters:

Sample 1: (fresh tissue) ViaDerm parameter setting: 2 applications; Electrodes: 140; Burst length: 700 μsec; Number of bursts: 5; TEWL control: 6.7 g/hm$^2$; TEWL after application(s): 28.2 g/hm$^2$.

Sample 2: (fresh tissue) ViaDerm parameter setting: 2 applications; Electrodes: 140; Burst length: 700 μsec; Number of bursts: 3; TEWL control: 6.2 g/hm$^2$; TEWL after application(s): 19.2 g/hm$^2$.

Sample 3: (frozen tissue) ViaDerm parameter setting: 2 applications; Electrodes: 140; Burst length: 700 μsec; Number of bursts: 5; TEWL control: 6.5 g/hm$^2$; TEWL after application(s): 9.3 g/hm$^2$.

Heat Separation:

Heat-separated epidermal membrane was prepared as described in Example 2.

Diffusion Assay:

Non-treated and ViaDerm-treated human epidermal membranes were placed on Type-1 filter paper (Whatman PLC, Maidstone, Kent) and mounted between donor and receptor compartments of static Franz-type glass diffusion cells. The compartments were sealed using silicone grease, and metal clips used to clamp the chambers tightly closed. The receptor phase of each cell, which had a precisely calibrated volume and diffusional area, was filled with Phosphate Buffered Saline (PBS; pH 7.4; Sigma Chemical Company, Poole, UK) and a magnetic flee was added to ensure thorough mixing. The receptor arm was sealed with a glass cap and the donor chamber was occluded with a cover slip to prevent sample evaporation. The cells were placed on a multipoint magnetic stirrer in a water-bath maintained at a constant temperature of 37° C., to provide continuous agitation and a skin surface temperature of 32° C. Prior to addition of the test formulations to the donor chamber, cells were allowed to equilibrate for at least 30 minutes and the integrity of epidermal membranes was visually inspected.

Fluorescently (FITC) labeled polystyrene nanospheres (L-1280; Sigma Chemical Company, Poole, UK) were added to the donor chambers of diffusion cells. In three of the cells the epidermal membranes had been pre-treated with 2 applications of ViaDerm. A positive control cell was prepared using filter paper alone. A negative control was prepared using a diffusion cell containing an untreated epidermal membrane.

A volume of 500 μl of a 10 μl/ml dilution of the fluorescent nanospheres stock suspension, concentration $4.57^{10}$/μl, was applied to the surface of the epidermal membrane. After 16 hrs the donor phase was transferred to a 96 well plate for analysis using a fluorescence spectrophotometer (BMG Fluostar, Aylesbury, UK) with excitation and emission wavelengths set at 485 and 520 nm, respectively. A calibration curve was performed using standard dilutions of the suspension of fluorescent nanoparticles (FIG. 4).

Transmission Electron Microscopy (TEM):

15 μl of a suspension of lipid:polycation:pDNA (LPD) complexes or fluorescent nanoparticles was placed onto 100 mesh nickel grids. After 3 min the excess solution was wicked off with filter paper and replaced with freshly filtered and centrifuged 2% aqueous uranyl acetate for 30 seconds. The grids were washed twice with distilled water, allowed to dry and imaged using a Philips 208 transmission electron microscope.

Results

Figure 6:
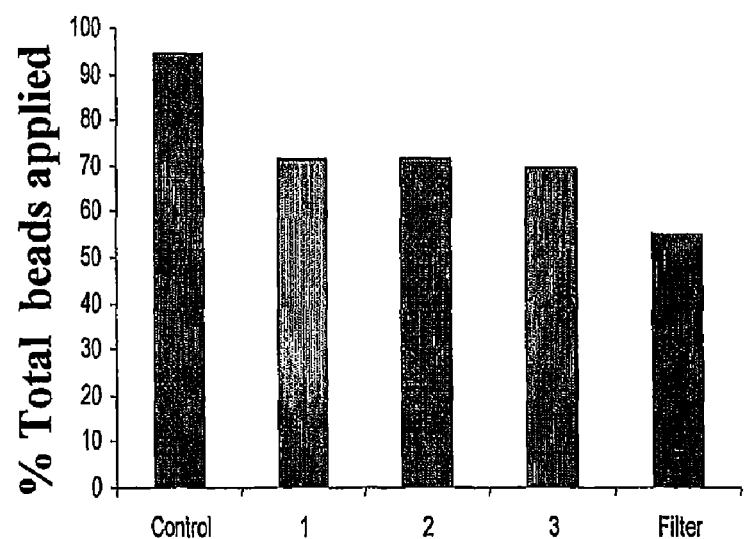
FIG. 6 shows the diffusion of fluorescent nanoparticles through ViaDerm-treated epidermal membranes. The data are presented as a percentage of total nanoparticles applied remaining in the donor phase after 16 hrs. Control, Non-treated epidermal membrane; 1, Epidermal membrane from fresh tissue treated with 2 applications of ViaDerm at parameter setting of 330V, 5 bursts, 700 µsec, 140 electrodes; 2, Epidermal membrane from fresh tissue treated with 2 applications of ViaDerm at parameter setting of 330V, 3 bursts, 700 µsec, 140 electrodes; 3, Epidermal membrane from defrosted tissue treated with 2 applications of ViaDerm at parameter setting of 330V, 5 bursts, 700 µsec, 140 electrodes; Filter, Filter paper only.

FIG. 5 illustrates the rationale for using spherical fluorescent nanoparticles as a diffusive model for LPD non-viral gene delivery vectors. FIG. 6 shows the diffusion of fluorescent nanoparticles through ViaDerm-treated epidermal membranes. As shown in FIG. 6, the untreated epidermal membrane sample (control) demonstrated a highly significant barrier function to 100 nm nanoparticles, with 94.3% of the applied nanoparticles still being recoverable in the donor phase after 16 hrs incubation. All of the ViaDerm-treated epidermal membranes demonstrated an increased and reproducible permeability to the nanoparticles, with between 28.5 and 30.4% of the applied nanoparticles leaving the donor compartment via the RF-micro-channels. This increase in diffusion of nanoparticles is considerable especially when compared with the positive control (filter). In the filter sample, 44.8% of the fluorescent nanoparticles were still present in the donor compartment reflecting the barrier properties of the underlying filter support. The transepidermal water loss (TEWL) data for the skin samples was intriguing. Despite the diffusion data showing comparable levels of permeation in the outer layers of the skin for both fresh and frozen tissue, the fresh skin experienced an increase in TEWL from 6.7 to 28.2 g/hm$^2$ when treated with the ViaDerm whereas previously frozen tissue showed a smaller increase from 6.5 to 9.3 g/hm$^2$ at the same parameter setting. This reduced increase in TEWL following application of ViaDerm was observed for other frozen samples and it was therefore decided to use freshly obtained unfrozen tissue for all subsequent experiments.

EXAMPLE 4

Visualization of Micro-Channels En face

The distribution pattern of RF-micro-channels in full-thickness human skin was detected.

Materials and Methods

Tissue:

Full-thickness human skin was obtained and prepared as described in Example 1.

Figure 7A:
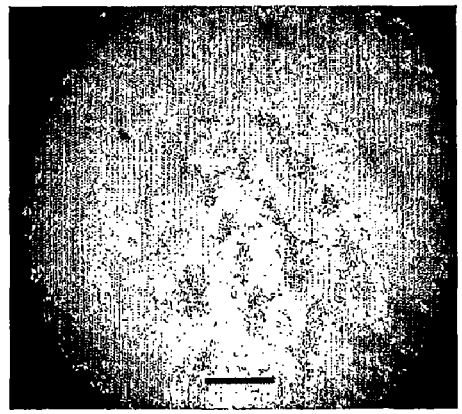
FIGS. 7A-C show stereomicrographs showing distribution pattern of RF-micro-channels in human skin. A, Untreated skin; B and C, ViaDerm-treated skin. Bar=500 µm.
Figure 7B:
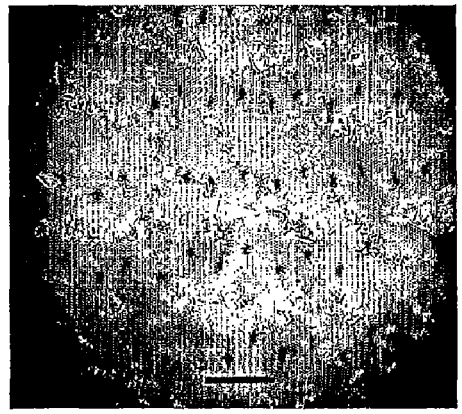

ViaDerm Parameters:

FIG. 7B: ViaDerm parameter setting: 2 applications; Electrodes: 140; Burst length: 700 μsec; Number of bursts: 5; TEWL control: 8.1 g/hm$^2$; TEWL after application(s): 18.0 g/hm$^2$.

Figure 7C:
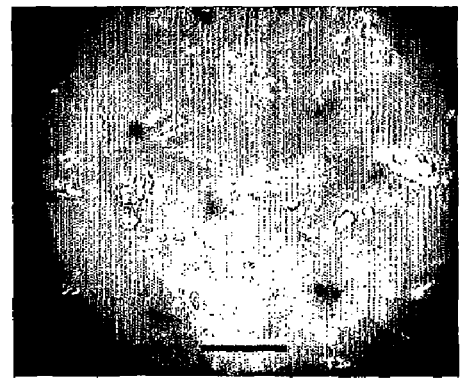

FIG. 7C: ViaDerm parameter setting: 2 applications; Electrodes: 140; Burst length: 700 μsec; Number of bursts: 5; TEWL control: 9.5 g/hm$^2$; TEWL after application(s): 22.0 g/hm$^2$.

FIG. 8: ViaDerm parameter setting: 1 application; Electrodes: 140; Burst length: 700 μsec; Number of bursts: 5; TEWL control: 6.8 g/hm$^2$; TEWL after application(s): 7.6 g/hm$^2$.

Sample Preparation:

Skin was incubated in media (MEM (EAGLES) 25 mM HEPES) for 24 hrs at 37° C. Following two washes in PBS the skin was fixed in 0.5% gluataraldehyde for 2 hrs on ice. For methylene blue staining, 5 drops of 1.5% methylene blue solution was applied to the surface of the ViaDerm treated skin for 5 min. Subsequently, excess stain was rinsed with PBS and the tissue surface was swabbed with 70% ethanol.

Stereomicroscopy:

Tissue was visualized using a Zeiss Stemi 2000C Stereomicroscope with a 2,0× attachment and an Scholt KL1500 electronic light source.

Light Microscopy:

Tissue stained with methylene blue was visualized using an Olympus BX50 microscope and an Scholt KL1500 electronic light source.

Results

FIG. 7B and FIG. 7C clearly demonstrate the distribution of micro-channels in ViaDerm treated skin. The brown discoloration of the channels observed in FIG. 7 suggests a change in the tissue properties surrounding the channel. The channels can also be visualized through their ability to uptake and retain methylene blue in solution (FIG. 8).

EXAMPLE 5

Histology of Sectioned Tissue

The depth and structural morphology of the micro-channels generated in ViaDerm-treated human skin were next tested.

Materials and Methods

Tissue:

Full-thickness human skin was obtained and prepared as described in Example 1.

Sample Preparation:

ViaDerm-treated skin was washed with PBS and fixed for 4 hrs in 0.5% gluataraldehyde on ice. Fixed tissue was embedded in OCT medium (RA Lamb Limited, Eastbourne, UK) on Cardice and sectioned using a Leica CM3050S Cryostat.

ViaDerm Parameters:

Parameter 3: ViaDerm parameter setting: 4 applications; Electrodes: 140; Burst length: 700 μsec; Number of bursts: 3; TEWL control: 4.0 g/hm$^2$; TEWL after application(s): 30.3 g/hm$^2$.

Parameter 5: ViaDerm parameter setting: 4 applications; Electrodes: 140; Burst length: 700 μsec; Number of bursts: 5; TEWL control: 6.7 g/hm$^2$; TEWL after application(s): 28.2 g/hm$^2$.

Parameter 6: ViaDerm parameter setting: 4 applications; Electrodes: 140; Burst length: 700 μsec; Number of bursts: 1; TEWL control: 5.5 g/hm$^2$; TEWL after application(s): 24.8 g/hm$^2$.

Parameter 7: ViaDerm parameter setting: 4 applications; Electrodes: 140; Burst length: 700 μsec; Number of bursts: 2; TEWL control: 5.2 g/hm$^2$; TEWL after application(s): 28.7 g/hm$^2$.

Parameter 10: ViaDerm parameter setting: 4 applications; Electrodes: 140; Burst length: 700 μsec; Number of bursts: 5; TEWL control: 6.5 g/hm$^2$; TEWL after application(s): 32.6 g/hm$^2$.

Tissue Staining:
   a) Eosin: Tissue sections were collected onto adhesive-coated Histobond® microscope slides (RA Lamb), immersed in 1% aqueous eosin solution (BDH Laboratory Supplies, Dorset, UK) for 5 seconds, rinsed with water and allowed to dry.
   b) Haematoxylin and Eosin (H&E): Tissue sections were collected onto Histobond® microscope slides, immersed in Harris' haematoxylin solution (BDH Laboratory Supplies) for 5 min, rinsed with water and allowed to dry. Post-staining with eosin was performed as described above.
   c) Toludine Blue: Tissue sections were collected onto Histobond® microscope slides, immersed in 1% aqueous toludine blue solution (TAAB Laboratories Equipment Limited, Berkshire, UK) for 5 min, rinsed with water and allowed to dry.

Results

Figure 10A:
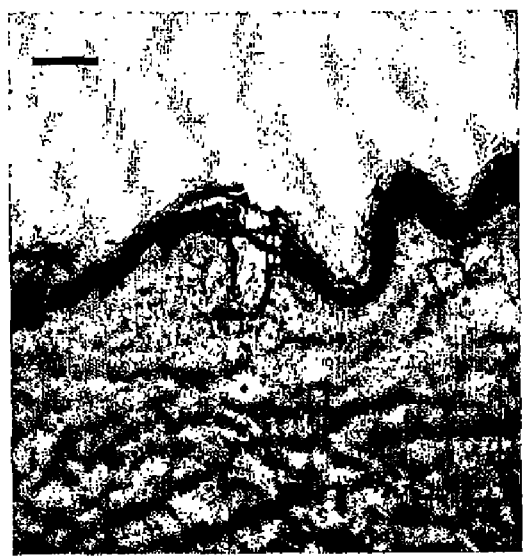
FIGS. 10A-B show light micrographs of human breast skin treated with ViaDerm parameter setting of 330V, 5 bursts, 700 µsec, 140 electrodes. A, H&E stained, original magnification=×100; B, H&E stained, original magnification=×200. Bar=100 µm.
Figure 10B:

FIG. 9 and FIG. 10 illustrate the dimensions of RF-micro-channels that are created in human breast skin following application of ViaDerm at different parameter settings. The photomicrographs presented are representative of the entire population of channels observed. In most cases the channels are approximately 100 μm in length and 30-50 μm at their widest aperture. The channels penetrate through the human epidermis and into the underlying dermis.

EXAMPLE 6

Co-Localization of Fluorescent Nanoparticles into Micro-Channels

The dimensions of the RF-micro-channels were determined in order to evaluate whether they are of sufficient size to permit penetration and retention of 100 nm fluorescent nanoparticles.

Materials and Methods

Tissue:

Full-thickness human skin was obtained and prepared as described in Example 1.

ViaDerm Parameters:

ViaDerm parameter setting: 4 applications; Electrodes: 140; Burst length: 700 μsec; Number of bursts: 5; TEWL control: 6.7 g/hm$^2$; TEWL after application(s): 46.0 g/hm$^2$.

Sample Preparation:

ViaDerm-treated skin was placed in a 6 well cell culture plate and maintained in 1.5 ml media (MEM (EAGLES) 25 mM HEPES). 50 μl of a concentrated ($4.57^{10}$/μl) stock of fluorescently (FITC) labeled polystyrene nanospheres (L-1280; Sigma Chemical Company, Poole, UK) was pipetted onto the treated skin surface and the sample was incubated for 6 hrs at 37° C. After 6 hrs, additional 2 ml of media were added to submerge the skin. The skin was incubated for a further 18 hrs. Following two washes in PBS the skin was fixed in 0.5% gluataraldehyde for 1 hr on ice. Fixed tissue was embedded in OCT medium (RA Lamb) on Cardice and sectioned using a Leica CM3050S Cryostat.

Staining/Visualization:

Sections were either stained with H&E and visualized as described in Example 5 or visualized unstained under blue fluorescence (Olympus BX50 microscope).

Results

Figure 11A:
FIGS. 11A-B show light and fluorescence photomicrographs of RF-micro-channels containing fluorescent nanoparticles. A, a light photomicrograph; B, a fluorescence photomicrograph. Original magnification=×100. Bar=100 µm.
Figure 11B:

FIG. 11 shows that the RF-micro-channels are of sufficient dimensions to uptake and entrap fluorescent nanoparticles with a diameter of 100 nm. The micro-channels are therefore of appropriate dimensions for the delivery of macromolecules and nanoparticles such as non-viral gene therapy vectors. Over the incubation period, many of the channels appear to have resealed at their surface to enclose the particles inside a 'drug delivery reservoir'.

EXAMPLE 7

Co-Localization of Fluorescently Labeled DNA into Micro-Channels

Figure 12A:
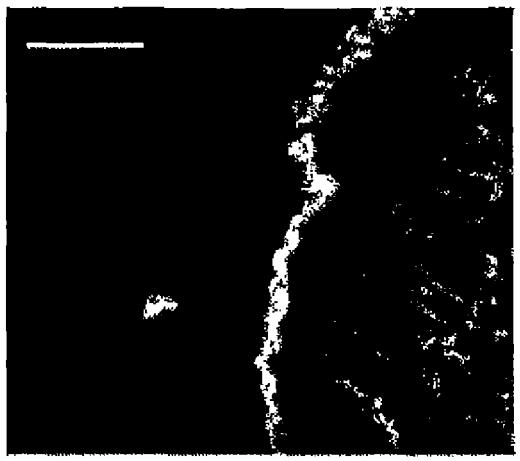
FIGS. 12A-D show fluorescence photomicrographs of ViaDerm-treated skin post-incubated with fluorescently labeled plasmid DNA alone. Original magnification=×200. Bar=100 µm.
Figure 12B:
Figure 12C:
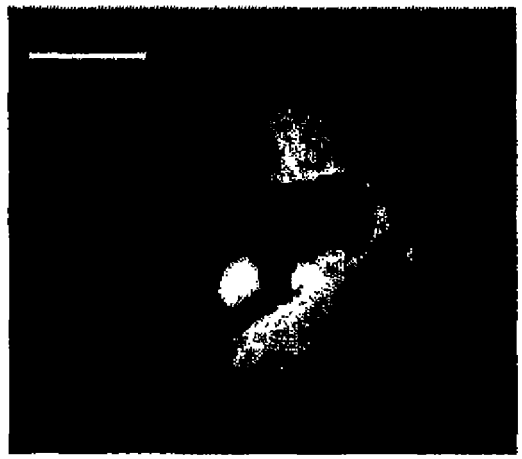
Figure 12D:
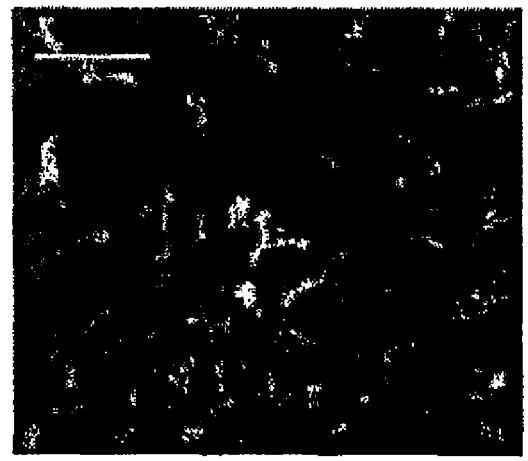
Figure 13A:
FIGS. 13A-F show double-labeling photomicrographs of ViaDerm-treated skin post-incubated with fluorescently labeled plasmid DNA in an LPD gene vector complex. A, C, and E, show light micrographs; B, D, and F, show fluorescence micrographs. Original magnification=×100. Bar=100 μm.
Figure 13B:
Figure 13C:
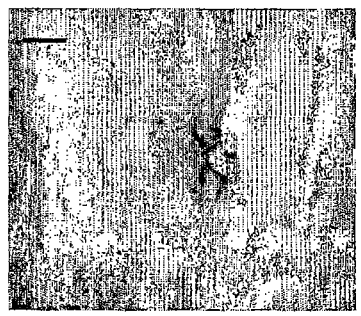
Figure 13D:
Figure 13E:
Figure 13F:
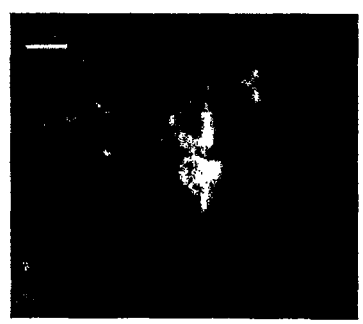

The aims of the following experiment were to determine whether the dimensions of the RF-micro-channels are of sufficient dimensions to allow penetration and retention of fluorescently labeled plasmid DNA, and to determine whether complexation of plasmid DNA with lipid and polycation affects the penetration and retention of fluorescently labeled plasmid DNA.
Materials and Methods
Tissue:
Full-thickness human skin was obtained and prepared as described in Example 1.
ViaDerm Parameters:
DNA alone: ViaDerm parameter setting: 2 applications; Electrodes: 140; Burst length: 700 μsec; Number of bursts: 5; TEWL control: 7.5 g/hm$^2$; TEWL after application(s): 14.2 g/hm$^2$.
LPD: ViaDerm parameter setting: 4 applications; Electrodes: 140; Burst length: 700 μsec; Number of bursts: 5; TEWL control: 5.3 g/hm$^2$; TEWL after application(s): 28.3 g/hm$^2$.
Sample Preparation:
Fluorescently labeled plasmid DNA was prepared by labeling pEGFP-N1 reporter plasmid with a rhodamine fluorophore using a LabelIT® Nucleic Acid Labeling Kit (Mirus Corporation, Madison, Wis.). ViaDerm-treated skin was placed in a 6 well cell culture plate and maintained in 1.5 ml media (MEM (EAGLES) 25 mM HEPES). 50 μl of labeled pDNA alone (containing 2 μg pDNA) or a suspension of LPD complexes comprising fluorescently labeled pDNA (5 μg) pre-complexed with protamine sulphate (10 μg; Grade X from salmon sperm; Sigma Chemicals, Poole, UK) and 1,2-Dioleoyl-3-Trimethylammonium-Propane (DOTAP) liposomes (15 μg; Avanti Polar Lipids, Alabama, USA) were pipetted onto the treated skin surface and the sample was incubated for 1 hr at 37° C. After 1 hr, additional 2 ml of media were added to submerge the skin. The skin was incubated for a further 47 hrs. Following two washes in PBS the skin was fixed in 0.5% glutaraldehyde for 1 hr on ice. Fixed tissue was embedded in OCT medium (RA Lamb) on Cardice and sectioned using a Leica CM3050S Cryostat.
Light/Fluorescence Microscopy:
Sections were visualized unstained under bright field or blue fluorescence (Olympus BX50 microscope).
Results
FIG. 12A shows the distribution of fluorescently labeled pDNA on a flat section of skin. FIG. 12B shows a fluorescent pDNA particle residing in a skin fold (note the stratum corneum is continuous and unbroken). FIG. 12C shows an RF-micro-channel. Interestingly, FIG. 12D shows the presence of a fluorescently labeled pDNA particle deep in the dermis of the same ViaDerm-treated tissue sample shown in FIG. 12C.
FIG. 13 shows that the fluorescence associated with the rhodamine labeled pDNA is not diminished by complexation with polycation and lipid into an LPD gene delivery vector. In these images the LPD vector is clearly seen to be localized both at the surface (FIGS. 13B and 13D) and inside (FIG. 13F) the RF-micro-channels.

EXAMPLE 8

β-Galactosidase Gene Expression in Heat-Separated Epidermal Membrane

It was next determined whether β-galactosidase reporter gene can be expressed in heat-separated epidermal membrane when lipid:polycation:pDNA (LPD) vectors are applied to skin pre-treated with ViaDerm.
Materials and Methods
Tissue:
Full-thickness human skin was obtained and prepared as described in Example 1.

ViaDerm Parameters:
ViaDerm parameter setting: 2 applications; Electrodes: 140; Burst length: 700 μsec; Number of bursts: 5; TEWL control: 6.0 g/hm$^2$; TEWL after application(s): 14.6 g/hm$^2$.
Sample Preparation:
ViaDerm-treated skin was placed in a 6 well cell culture plate and maintained in 1.5 ml media (MEM (EAGLES) 25 mM HEPES). pCMVβ plasmid DNA, expressing the β-galactosidase reporter gene under the control of the human cytomegalovirus immediate early (CMV IE) promoter, was obtained from ClonTech Laboratories Inc. (Palo Alto, USA), propagated using a transformed DH5α strain of *Eschericia coli* colonized onto an ampicillin selective LB agar plate and cultured overnight at 37° C. The pDNA was harvested and purified using a Qiagen Plasmid Mega Kit (Qiagen, Crawley, UK).
A 300 μl suspension of lipid:polycation:pDNA (LPD) vectors was prepared containing 50 μg pCMVβ plasmid DNA, 100 μg protamine sulphate (Grade X from salmon sperm) and 150 μg DOTAP liposomes. LPD complexes were prepared by sequential addition (with 10 min incubation at each step) of firstly protamine (1 mg/ml stock in sterile purified water) and then extruded DOTAP liposomes to pDNA (1 mg/ml stock in TE buffer) to achieve a lipid:protamine:pDNA mass (w/w) ratio of 3:2:1. 100 μl of the LPD suspension was pipetted onto the ViaDerm-treated skin surface and the sample was incubated for 18 hrs at 37° C. At 18 hrs, additional 2 ml of media were added and the submerged skin was incubated for a further 30 hrs.
X-gal Staining:
After two washes in PBS, the skin was fixed on ice in 0.5% glutaraldehyde for 1 hr and stained for β-galactosidase activity over 24 hrs using a LacZ Reporter Assay Kit for Tissue Staining (In-Vivogen, San Diego, Calif.). After two additional washes in PBS, the skin was heat-separated as described in Example 2.
Light Microscopy:
The heat-separated epidermal membrane was visualized using an Olympus BX50 microscope.
Results
FIG. 14 shows the appearance of micro-channels in heat-separated epidermal membrane. The brown discoloration observed previously in Example 4 is once again apparent. The boundary, and possibly the center, of the channel are colored blue. Under the enzymatic assay conditions blue coloration is associated with the presence of the reporter gene product, β-galactosidase.

EXAMPLE 9

β-Galactosidase Gene Expression En Face

It was then determined whether β-galactosidase reporter gene can be delivered to, and expressed in, full-thickness skin after application of the ViaDerm device.
Materials and Methods
Tissue:
Full-thickness human skin was obtained and prepared as described in Example 1.
ViaDerm Parameters:
ViaDerm parameter setting: 2 applications; Electrodes: 140; Burst length: 700 μsec; Number of bursts: 5; TEWL control: 10.3 g/hm$^2$; TEWL after application(s): 26.2 g/hm$^2$.
Sample Preparation:
ViaDerm-treated skin was placed in a 6 well cell culture plate and maintained in 1.5 ml media (MEM (EAGLES) 25 mM HEPES). 100 μl of pCMVβ plasmid DNA solution (1 mg/ml) was pipetted onto the ViaDerm-treated skin surface and the sample was incubated for 24 hrs at 37° C. Following two washes in PBS the stratum corneum of the skin was removed by tape stripping 20 times with D-Squame adhesive tape (CuDerm Corp., Dallas, Tex).

X-Gal Staining:

The tissue was fixed on ice in 0.5% glutaraldehyde for 1 hr, rinsed overnight in PBS and stained for β-galactosidase expression over 48 hrs using a LacZ Reporter Assay Kit for Tissue Staining, (Invivogen, San Diego, Calif.).

Light Microscopy:

The surface of the tape-stripped skin was visualized using an Olympus BX50 microscope and an Scholt KL1500 electronic light source.

Results

FIG. 15 shows the presence of expressed β-galactosidase in the RF-micro-channels. The skin was tape-stripped following application of the ViaDerm device and the DNA solution to allow more stain to reach the appropriate area of the tissue. In this experiment the plasmid was used alone, i.e., without any non-viral carrier system, as numerous studies have shown the ability of naked DNA to be expressed efficiently in vivo (e.g. Hengge, U.R. et al. Nature Genet 10: 161, 1995; Hengge, U.R. et al. J. Clinical Investigation, 97: 2911, 1996; and Chesnoy, S. and Huang, L. Molecular Therapy, 5: 57, 2002).

EXAMPLE 10

Histology of Sectioned Tissue

A comparison between micro-channels generated in a human skin after application of the ViaDerm™ device using 100-micron length electrodes or 50-micron length electrodes was performed.

Materials and Methods

Tissue:

Full-thickness human breast skin was obtained as described in Example 1.

ViaDerm Parameters:

Parameter 1: ViaDerm parameter setting: 4 applications; an electrode array containing 100-micron length electrodes; Electrodes: 140; Burst length: 700 μsec; Number of bursts: 1; TEWL control: 7.4 g/hm$^2$; TEWL after application(s): 10.7 g/hm$^2$.

Parameter 6: ViaDerm parameter setting: 4 applications; an electrode array containing 50-micron length electrodes; Electrodes: 140; Burst length: 700 g/hm$^2$; Number of bursts: 1; TEWL control: 5.7 g/hm$^2$; TEWL after application(s): 8.7 g/hm$^2$.

Sample Preparation:

ViaDerm-treated skin was washed with PBS, fixed for 2.5 hrs in 0.5% glutaraldehyde on ice and post-rinsed with PBS. Fixed tissue was embedded in OCT medium (RA Lamb Limited, Eastbourne, UK) on Cardice and sectioned using a Leica CM3050S Cryostat.

Tissue Staining:

Eosin: Tissue sections were collected onto adhesive-coated Histobond® microscope slides (RA Lamb), immersed in 1% aqueous eosin solution (BDH Laboratory Supplies, Dorset, UK) for 5 seconds, rinsed with water and allowed to dry.

Toludine Blue: Tissue sections were collected onto Histobond® microscope slides, immersed in 1% aqueous toludine blue solution (TAAB Laboratories Equipment Limited, Berkshire, UK) for 5 min, rinsed with water and allowed to dry.

Results

The photomicrographs presented are representatives of the entire population of channels observed. In most cases the channels were approximately 50-100 μm in length and 30-50 μm at their widest aperture.

Figure 16A:
FIGS. 16A-B show light micrographs of human breast skin treated with ViaDerm. A, 100-micron length electrodes, Eosin stained, Original magnification=×100; B, 50-micron length electrodes, Toludine blue stained, Original magnification=×200. Bar=100 μm.
Figure 16B:
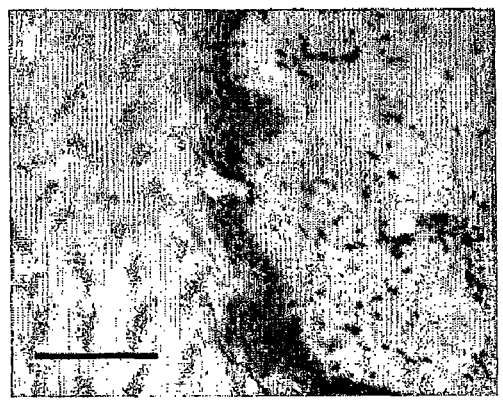
Figure 17A:
FIG. 17A-F show stereomicrographs of human skin stained for β-galactosidase expression after ViaDerm application, DNA coating and then an additional ViaDerm application. A-E, ViaDerm (50-micron length electrodes)-treated skin incubated with pCMVβ DNA; F, ViaDerm-treated skin incubated with PBS. Bar=1 mm.
Figure 17B:
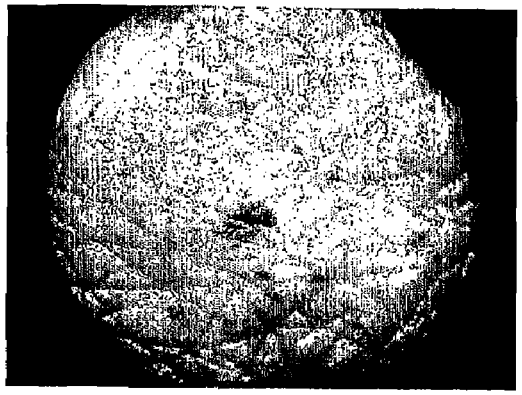
Figure 17C:
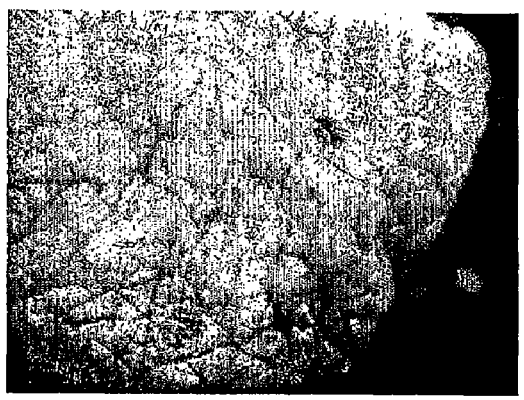
Figure 17D:
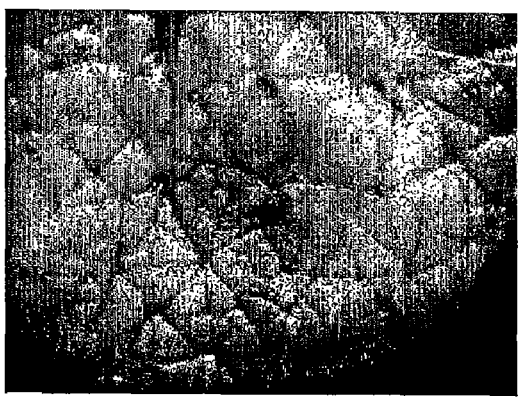
Figure 17E:
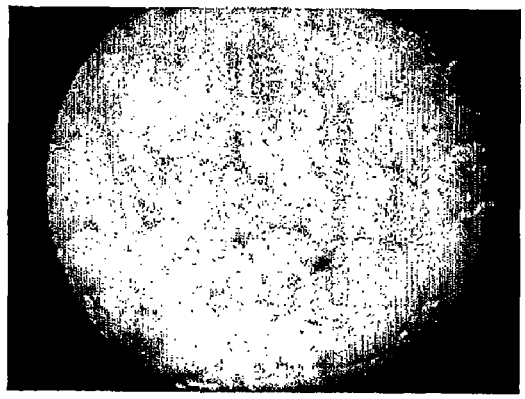
Figure 17F:
Figure 19A:
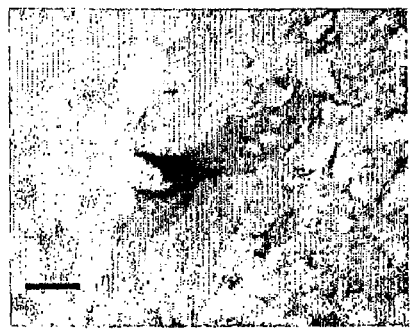
FIG. 19A-H show light photomicrographs of β-galactosidase stained tissue sections from skin treated successively with ViaDerm, DNA coating, and then with ViaDerm. A, Original magnification=×100; B, Original magnification=×200; C, Original magnification=×100; D, Original magnification=×100; E, Original magnification=×200; F, Original magnification=×200; G, Original magnification=×100. H, Original magnification=×100. Bar=100 μm.
Figure 19B:
Figure 19C:
Figure 19D:
Figure 19E:
Figure 19F:
Figure 19G:
Figure 19H:

The difference in the micro-channels generated by the 50 or 100-micron length electrode arrays is demonstrated in FIG. 16. In Examples 1 to 9 disclosed herein above, the 100-micron length electrode array generated micro-channels that penetrated through the human epidermis and into the underlying dermis (FIG. 16A). In contrast, the 50-micron length electrode array generated micro-channels that often resided solely in the viable epidermis (FIG. 16B). On the basis of these results, an electrode array containing 50-micron length electrodes was selected for further studies assessing gene expression in the epidermis.

The TEWL data further confirms the divergent morphology of the channels created using the 50 and 100-micron arrays (Table 1).

TABLE 1

Increase in trans-epidermal water loss (TEWL) following four applications of ViaDerm at parameter setting 6.

| Array | TEWL: Control (g/m$^2$hr) | TEWL: After ViaDerm (g/m$^2$hr) | TEWL (Increase) (%) |
|---|---|---|---|
| 50 micron | 5.7 | 8.7 | +3.0 |
| 100 micron | 5.5 | 24.8 | +19.3 |

EXAMPLE 11

β-Galactosidase Gene Expression En Face

The aim of the experiment was to determine whether β-galactosidase reporter gene can be delivered to, and expressed in, human skin after application of the ViaDerm device containing the 50-micron length electrodes.

Materials and Methods

Tissue:

Full-thickness human skin was transported on ice in DMEM 25 mM HEPES growth media (Invitrogen Corporation, Paisley, UK) supplemented with 5% fetal bovine serum and 1% penicillin/streptomycin. Split-thickness skin was prepared by removing a substantial proportion of the dermis by dissection.

ViaDerm Parameters:

Two applications pre- and 1 application post-DNA application; An electrode array containing 50-micron length electrodes; Electrodes: 140; Burst length: 700 μsec; Number of bursts: 1; TEWL control: g/hm$^2$.

Sample Preparation:

ViaDerm-treated skin was maintained at an air-liquid interface by placing on lens tissue supported by metal gauze in a 6 well cell culture plate containing 2.5 ml media (DMEM 25 mM HEPES supplemented with 5% fetal bovine serum and 1% penicillin/streptomycin) per well. Fifty μl of pCMVβ plasmid DNA solution (1 mg/ml) was pipetted and spread onto the ViaDerm-treated skin surface and the ViaDerm re-applied. Samples were incubated for 24 hrs at 37° C. After one wash in PBS/MgCl$_2$ (30 minutes), the tissue was fixed for 2 hr in 2% glutaraldehyde/MgCl$_2$ at 4° C. Subsequently the tissue was rinsed in a series of PBS/MgCl$_2$ solutions for 2 hr, 3 hr and 30 minutes.

X-Gal Staining:

The tissue was stained for β-galactosidase expression over 20 hrs using X-Gal staining solution [X-Gal (5% v/v of a 40 mg/ml solution in dimethylformamide, Fisher Scientific UK), Potassium ferricyanide (0.84% v/v of a 0.6 M solution, Sigma-Aldrich, UK), Potassium ferrocyanide (0.84% v/v of a 0.6M solution), Magnesium chloride (0.2% v/v of a 1 M solution, Sigma-Aldrich, UK), Tris HCl buffer pH8.5 (50% v/v of a 0.2 M solution, Fischer Scientific UK), Demonized water to 100%].

Stereomicroscopy:

Tissue was visualized using a Zeiss Stemi 2000C Stereomicroscope with a 2,0× attachment and a Scholt KL1500 electronic light source.

Light Microscopy:

The surface of the skin was visualized using an Olympus BX50 microscope and a Scholt KL1500 electronic light source.

Results

FIGS. 17 and 18 clearly demonstrate the presence of expressed β-galactosidase in the ViaDerm-treated skin. In this experiment the plasmid was used alone, i.e., without any non-viral carrier system as previous studies have shown the ability of naked DNA to be expressed efficiently in vivo (Hengge, U. R. et al. Nat. Genet. 10: 161, 1995; Hengge, U.R., et al. J. Clin. Invest. 97: 2911, 1996; and Chesnoy, S. et al. Mol. Therapy 5: 57, 2002). Best results in terms of β-galactosidase expression were obtained when the skin was treated successively with ViaDerm, DNA application, and then ViaDerm again. The device may therefore not only create micro-channels in skin but also drive the intracellular uptake of DNA.

EXAMPLE 12

β-Galactosidase Gene Expression in Sectioned Tissue

The pattern of β-galactosidase reporter gene expression in ViaDerm-treated skin was next determined.

Materials and Methods

Cryo-Sectioning:

The samples from Section 3 shown in FIGS. 17 and 18 were embedded in OCT medium (RA Lamb Limited, Eastbourne, UK) on Cardice and sectioned using a Leica CM3050S Cryostat.

Light Microscopy:

The tissue sections were visualized using an Olympus BX50 microscope.

Results

FIG. 19 clearly shows the presence of intense staining, relating to appreciable reporter gene expression, in the viable epidermal cells surrounding the RF-micro-channel. The staining is primarily localized to the epidermis.

Thus, these results demonstrate that the RF-micro-channels generated in human breast skin after application of the ViaDerm device containing the 50-micron electrode array are of appropriate dimensions to permit the delivery of plasmid DNA to skin. In addition, when ViaDerm is applied to skin that has been pre-coated with a solution of DNA the uptake and expression of the gene appears to be enhanced. The intense gene expression is primarily localized to the viable epidermis region of the tissue.

It will be appreciated by persons skilled in the art that the present invention is not limited by what has been particularly shown and described herein above. Rather the scope of the invention is defined by the claims that follow.

The invention claimed is:

1. A method for intradermal or transdermal delivery of an oligonucleotide or polynucleotide comprising:
    (a) generating a first plurality of micro-channels in an area of the skin of a subject;
    (b) after step (a), applying to the area of the skin of the subject where the first plurality of micro-channels are present a pharmaceutical composition comprising as an active ingredient a therapeutically effective amount of an oligonucleotide or polynucleotide and a pharmaceutically acceptable carrier; and
    (c) after step (b), generating a second plurality of micro-channels in said area of the skin of said subject, thereby facilitating the intradermal or transdermal delivery of the oligonucleotide or polynucleotide.

2. The method according to claim 1, wherein the oligonucleotide or polynucleotide is selected from the group consisting of oligonucleotides or polynucleotides of DNA, RNA, and synthetic analogs thereof.

3. The method according to claim 2, wherein the oligonucleotide or polynucleotide encodes a polypeptide, an analog, fragment, or fusion protein thereof.

4. The method according to claim 2, wherein the oligonucleotide or polynucleotide is operably linked to regulatory sequences, thereby capable of being expressed in cells of the subject.

5. The method according to claim 3, wherein the polypeptide is selected from the group consisting of insulin, proinsulin, follicle stimulating hormone, insulin like growth factor-1, insulin like growth factor-2, platelet derived growth factor, epidermal growth factor, fibroblast growth factors, nerve growth factor, colony stimulating factors, transforming growth factors, tumor necrosis factor, calcitonin, parathyroid hormone, growth hormone, bone morphogenic protein, erythropoietin, hemopoietic growth factors, luteinizing hormone, glucagon, glucagon like peptide-1, clotting factors, anti-clotting factors, atrial natriuretic factor, plasminogen activators, bombesin, thrombin, enkephalinase, vascular endothelial growth factor, anti-angiogenic factors, interleukins, viral antigens, non-viral antigens, transport proteins, and antibodies.

6. The method according to claim 2, wherein the oligonucleotide is selected from the group consisting of antisense oligonucleotides, small interfering oligonucleotides (siRNAs), and miRNAs.

7. The method according to claim 1, wherein the pharmaceutical composition further comprising at least one additive selected from the group consisting of lipids, polycations, and nuclease inhibitors.

8. The method according to claim 1, wherein generating the first and second plurality of micro-channels in the area of the skin of the subject is sequentially conducted with an apparatus comprising:
    (a) an electrode cartridge comprising a plurality of electrodes; and
    (b) a main unit comprising a control unit which is adapted to apply electrical energy between two or more electrodes when the electrodes are in vicinity of the skin, typically generating current flow or one or more sparks, enabling ablation of stratum corneum in an area beneath said electrodes, thereby generating the first and second plurality of micro-channels.

9. The method according to claim 8, wherein the electrode cartridge is adapted to generate a plurality of micro-channels of uniform shape and dimensions.

10. The method according to claim 8, wherein the electrodes have a diameter in a range of 30 to 150 microns.

11. The method according to claim 10, wherein the electrodes have a diameter in a range of 40 to 100 microns.

12. The method according to claim 8, wherein the electrodes have a length in a range of 30 to 500 microns.

13. The method according to claim 12, wherein the electrodes have a length in a range of 50 to 100 microns.

14. The method according to claim 8, wherein the electrical energy is of radio frequency.

* * * * *